(12) United States Patent
Pfizenmaier et al.

(10) Patent No.: US 8,404,238 B2
(45) Date of Patent: Mar. 26, 2013

(54) HUTNFR1 SELECTIVE ANTAGONISTS

(75) Inventors: Klaus Pfizenmaier, Tiefenbronn (DE); Peter Scheurich, Stuttgart (DE); Roland Kontermann, Ebsdorfergrund (DE); Sabine Münkel, Gärtringen (DE)

(73) Assignee: Universitaet Stuttgart (DE)

( * ) Notice: Subject to any disclaimer, the term of this patent is extended or adjusted under 35 U.S.C. 154(b) by 408 days.

(21) Appl. No.: 12/531,000

(22) PCT Filed: Mar. 13, 2008

(86) PCT No.: PCT/EP2008/002033
§ 371 (c)(1),
(2), (4) Date: Feb. 23, 2010

(87) PCT Pub. No.: WO2008/113515
PCT Pub. Date: Sep. 25, 2008

(65) Prior Publication Data
US 2010/0150916 A1 Jun. 17, 2010

Related U.S. Application Data

(60) Provisional application No. 60/918,892, filed on Mar. 19, 2007.

(30) Foreign Application Priority Data

Mar. 19, 2007 (EP) .................................... 07005603

(51) Int. Cl.
*A61K 39/395* (2006.01)
*C07K 16/28* (2006.01)
(52) U.S. Cl. ............... 424/143.1; 424/141.1; 530/388.1; 530/388.22
(58) Field of Classification Search .................. None
See application file for complete search history.

(56) References Cited

U.S. PATENT DOCUMENTS 5,736,138 A 4/1998 Pfizenmaier et al.
2008/0008713 A1* 1/2008 Brewis ....................... 424/143.1

FOREIGN PATENT DOCUMENTS

| EP | 0444560 | | 9/1991 |
| EP | 0444560 | A1 | 9/1991 |
| WO | 2007/049017 | A2 | 5/2007 |
| WO | WO 2007/049017 | | 5/2007 |

OTHER PUBLICATIONS

Rudikoff, Giusti, Cook, and Scharff. Single amino acid substitutions altering antigen binding specificity. Proceedings of the National Academy of Science, 1982. vol. 79, p. 1979.*
Mac Callum, Martin, and Thornton. Antigen antibody interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*
Wu, Nie, Huse, and Watkins. Humanization of a murine monoclonal antibody by simultaneous optimization of framework and CDR residues. Journal of Molecular Biology, 1999. vol. 294, pp. 151-162.*
Vajdos, Adams, Breece, Presta, De Vos, and Sidhu. Comprehensive functional maps of the antigen-binding site of an Anti-ErbB2 antibody obtained with shotgun scanning mutagenesis. Journal of Molecular Biology, 2002. vol. 320, pp. 415-428.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Aggarwal, Nat. Rev Immunol. 3: 745-756 (2003).
Arnett et al., Nat. Neurosci. 4: 1116-1122 (2001).
Boado et al., Bioconjung. Chem., Epub ahead of press (2007).
Chatzantoni, Curr. Top. Med. Chem. 6: 1707-1714 (2006).
Fontaine et al., J. Neurosci. 22, RC216 (2002).
Grell et al., Cell 83: 793-802 (1995).
Grell et al., EMBO J. 18: 3034-3043 (1999).
Hellendorn et al., Cancer Cell International 4 (Spl.1), 20 (2004).
Hotamisligil, Nature 444: 860-867 (2006).
Hwang et al., Methods: A Companion to Methods in Enzymology, Academic Press Inc., N.Y., 36(1): 35-42 (2005).
Jespers et al., Biotechnology, Nature Publishing Co. New York 12(9): 899-903 (1994).
Jones et al., Nature 321: 522-525 (1986).
Kashmiri et al., Methods 36: 25-34 (2005).
Kassiotis, J. Exp. Med. 193: 427-434 (2001).
Kollias et al., Curr. Dir. Autoimmun. 5: 30-50 (2002).
Komata et al., Tissue Antigens, 53: 527-533 (1999).
Kontermann et al., Journal of Immunotherapy 31(3): 225-234 (2008).
Kusters et al., Eur. J. Immunol. 27: 2870-2875 (1997).

(Continued)

*Primary Examiner* — David Romeo
(74) *Attorney, Agent, or Firm* — Perkins Coie LLP

(57) ABSTRACT

The present invention relates to a ligand, which specifically binds to human tumor necrosis factor type 1 receptor (huTNFR1). The ligand includes one or more amino acid sequences of human origin capable of reducing the immunogenic response of the ligand in humans and one or more amino acid sequences capable of selectively binding to huTNFR1. The present invention also relates to a nucleic acid sequence encoding the ligand and to a pharmaceutical composition for the treatment of disorders related to huTNFR1.

9 Claims, 9 Drawing Sheets

OTHER PUBLICATIONS

Figure 3:
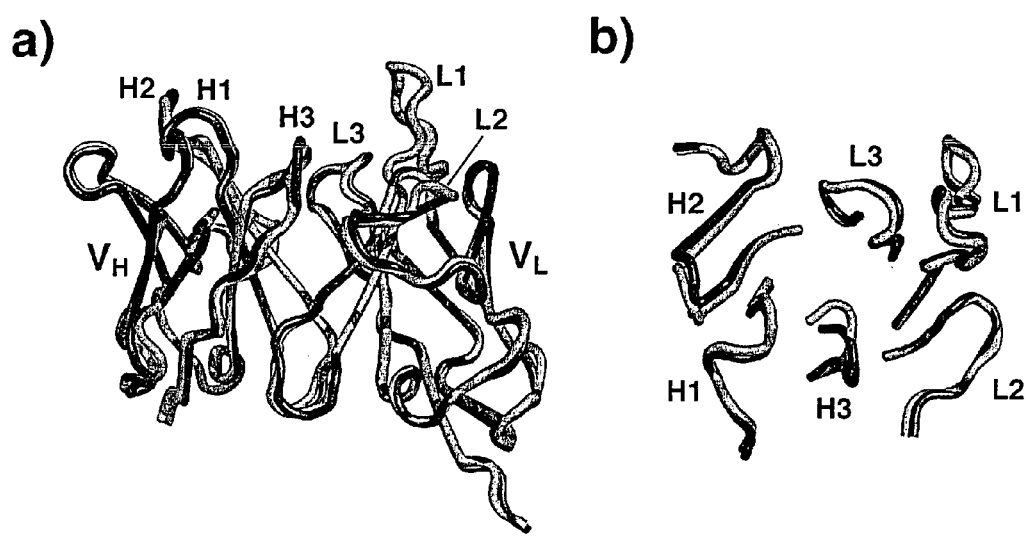
Figure 4:
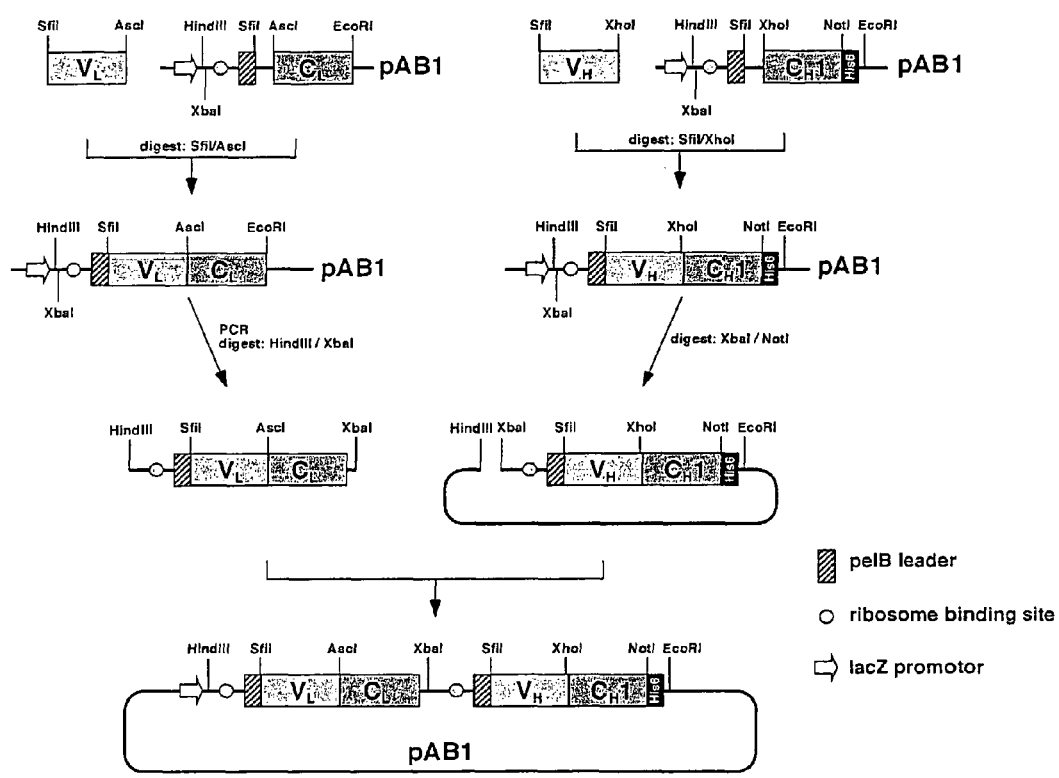

Lo, Antibody engineering, methods and protocols, Humana Press, p. 135-159 (2004).
Locksley et al., Cell 104: 487-501 (2001).
Luo et al., Antibody engineering methods and protocols, Humana Press, Towota, p. 135-159 (2004).
Marchetti et al., J. Biol. Chem., 2004, No. 279, p. 32869-32881.
Moosmayer et al., Ther. Immunol., 2: 31-40 (1995).
Owens et al., Nat. Med. 7: 161-166 (2001).
Roguska et al., Proc. Natl. Acad. Sci. USA 91: 969-973 (1994).
Van der Meer, Am. J. Physiol. Regul. Integr. Comp. Physiol. 292: R86-R98 (2007).
Storz et al., FEBS Lett. 440: 41-45 (1998).
Thoma et al., J. Exp. Med. 172: 1019-1023 (1990).
Ueki et al., Cell 128: 71-83 (2007).
Whitelegg, Web. Prot. Eng. 13: 819-824 (2000).
Moosmayer, D., et al., "A single-chain TNF receptor antagonist is an effective inhibitor or TNF mediated cytotoxicity", Therapeutic Immunology, Feb. 1995, 2(1):31-40.
Hwang, W.Y.K., et al., "Use of human germline genes in a CDR homology-based approach to antibody humanization", Methods, May 2005, 36(1):35-42.
Jespers, L.S., et al., "Guiding the Selection of Human Antibodies from Phage Display Repertoires to a Single Epitope of an Antigen", Bio/Technology, Sep. 1, 1994, 12(9):899-903.
Kontermann, R.E., et al., "A Humanized Tumor Necrosis Factor Receptor 1 (TNFR1)-specific Antagonistic Antibody for Selective Inhibition of Tumor Necrosis Factor (TNF) Action", Journal of Immunotherapy, Apr. 2008, 31(3):225-234.

* cited by examiner

V_H

```
                   FR1                  CDRH1      FR2              CDRH2
H398-VH     QVQLQESGAELARPGASVKLSCKAS GYTFTDFYIN WVKQRTGQGLE WIGEIYPYSGHAYYNEKFKA
IZI-06.1 VH QVQLVQSGAEVKKPGSSVKVSCKAS GYTFTDFYIN WVRQAPGQGLE WIGEIYPYSGHAYYNEKFKA
VH1-69      QVQLVQSGAEVKKPGSSVKVSCKAS GGTFSSYAIS WVRQAPGQGLE WMGGIIPIFGTANYAQKFQG
              **   ***   *    *       *  * ****  *  **    *  *  ** *  * ** **

FR3                    CDRH3    FR4
H398-VH     KATLTADKSSSTAFMQLNSLTSEDSAVYFCVR WDFLDY WGQGTTLTVSS
IZI-06.1 VH RVTITADKSTSTAYMELSSLRSEDTAVYYCAR WDFLDY WGQGTTVTVSS
VH1-69      RVTITADKSTSTAYMELSSLRSEDTAVYYCAR
              ** *       *   * ****  *     * *
```

V_L

```
                   FR1                  CDRL1      FR2              CDRL2
H398-VL     DIVMTQSPLSLPVSLGDQASISC RSSQSLLHSNGNTYLHWY VQKPGQSPK LLIYTVSNRFS
IZI-06.1 VL DIVMTQSPLSLPVTPGEPASISC RSSQSLLHSNGNTYLHWY LQKPGQSPQ LLIYTVSNRFS
A3          DIVMTQSPLSLPVTPGEPASISC RSSQSLLHSNGYNYLDWY LQKPGQSPQ LLIYLGSNRAS
                         ** **              **  *  *         *    **   *

FR3                    CDRL3     FR4
H398-VL     GVPDRFSGSGSGTDFTLKISRVEAEDLGVYFC SQSTHVPYT FGGGTKLEIKR
IZI-06.1 VL GVPDRFSGSGSGTDFTLKISRVEAEDVGVYYC SQSTHVPYT FGGGTKVEIKR
A3          GVPDRFSGSGSGTDFTLKISRVEAEDVGVYYC MQALQTP
                                             *   *   * ****
```

Fig. 1

IZI-06.1 VH

```
        KpnI          SfiI
  1   GGT ACC GCG GCC CAG CCG GCC ATG GCC CAG GTT CAG CTG GTT CAG AGC GGT GCG GAA GTG
       G   T   A   A   Q   P   A   M   A   Q   V   Q   L   V   Q   S   G   A   E   V

61   AAA AAA CCG GGC AGC AGC GTG AAA GTG AGC TGC AAA GCG AGC GGC TAT ACC TTT ACC GAT
       K   K   P   G   S   S   V   K   V   S   C   K   A   S   G   Y   T   F   T   D

121   TTC TAC ATT AAC TGG GTG CGT CAG GCA CCG GGT CAG GGC CTG GAA TGG ATT GGC GAA ATT
       F   Y   I   N   W   V   R   Q   A   P   G   Q   G   L   E   W   I   G   E   I

181   TAT CCG TAT AGC GGC CAT GCA TAT TAC AAC GAA AAA TTC AAA GCG CGT GTG ACC ATT ACC
       Y   P   Y   S   G   H   A   Y   Y   N   E   K   F   K   A   R   V   T   I   T

241   GCG GAT AAA AGC ACC AGC ACC GCG TAT ATG GAA CTG AGC AGC CTG CGT AGC GAA GAT ACC
       A   D   K   S   T   S   T   A   Y   M   E   L   S   S   L   R   S   E   D   T

301   GCG GTG TAT TAT TGC GCG CGT TGG GAT TTT CTG GAT TAT TGG GGC CAG GGC ACC ACC GTT
       A   V   Y   Y   C   A   R   W   D   F   L   D   Y   W   G   Q   G   T   T   V

XhoI       SacI
361   ACG GTC TCG AGT GAG CTC
       T   V   S   S   E   L
```

IZI-06.1 VL

```
        KpnI          SfiI
  1   GGT ACC GCG GCC CAG CCG GCC ATG GCC GAT ATT GTG ATG ACC CAG AGC CCG CTG TCT CTG
       G   T   A   A   Q   P   A   M   A   D   I   V   M   T   Q   S   P   L   S   L

61   CCG GTC ACG CCG GGT GAA CCG GCG AGC ATT AGC TGC CGT AGC AGC CAG AGC CTG CTG CAT
       P   V   T   P   G   E   P   A   S   I   S   C   R   S   S   Q   S   L   L   H

121   AGC AAC GGC AAC ACC TAT CTG CAT TGG TAT CTG CAG AAA CCG GGC CAG AGC CCG CAG CTG
       S   N   G   N   T   Y   L   H   W   Y   L   Q   K   P   G   Q   S   P   Q   L

181   CTG ATT TAT ACC GTG AGC AAC CGT TTT AGC GGC GTG CCG GAT CGC TTT AGC GGC AGC GGT
       L   I   Y   T   V   S   N   R   F   S   G   V   P   D   R   F   S   G   S   G

241   AGC GGC ACC GAT TTT ACC CTG AAA ATT AGC CGT GTG GAA GCG GAA GAT GTG GGC GTG TAT
       S   G   T   D   F   T   L   K   I   S   R   V   E   A   E   D   V   G   V   Y

301   TAT TGC AGC CAG AGC ACC CAT GTG CCG TAT ACC TTT GGC GGT GGC ACC AAA GTG GAA ATT
       Y   C   S   Q   S   T   H   V   P   Y   T   F   G   G   G   T   K   V   E   I

AscII      SacI
361   AAA CGT GGC GCG CCA GAG CTC
       K   R   G   A   P   E   L
```

Fig. 2

Figs. 7 a to f

```
                         SEQUENCE LISTING

<160> NUMBER OF SEQ ID NOS: 17

<210> SEQ ID NO 1
<211> LENGTH: 10
<212> TYPE: PRT
<213> ORGANISM: Mus musculus

<400> SEQUENCE: 1

Gly Tyr Thr Phe Thr Asp Phe Tyr Ile Asn
1               5                   10

<210> SEQ ID NO 2
<211> LENGTH: 20
<212> TYPE: PRT
<213> ORGANISM: Mus Musculus

<400> SEQUENCE: 2

Trp Ile Gly Glu Ile Tyr Pro Tyr Ser Gly His Ala Tyr Tyr Asn Glu
1               5                   10                  15

Lys Phe Lys Ala
            20

<210> SEQ ID NO 3
<211> LENGTH: 6
<212> TYPE: PRT
<213> ORGANISM: Mus Musculus

<400> SEQUENCE: 3

Trp Asp Phe Leu Asp Tyr
1               5

<210> SEQ ID NO 4
<211> LENGTH: 18
<212> TYPE: PRT
<213> ORGANISM: Mus Musculus

<400> SEQUENCE: 4

Arg Ser Ser Gln Ser Leu Leu His Ser Asn Gly Asn Thr Tyr Leu His
1               5                   10                  15

Trp Tyr
```

```
<210> SEQ ID NO 5
<211> LENGTH: 11
<212> TYPE: PRT
<213> ORGANISM: Mus Musculus

<400> SEQUENCE: 5

Leu Leu Ile Tyr Thr Val Ser Asn Arg Phe Ser
1               5                   10

<210> SEQ ID NO 6
<211> LENGTH: 9
<212> TYPE: PRT
<213> ORGANISM: Mus Musculus

<400> SEQUENCE: 6

Ser Gln Ser Thr His Val Pro Tyr Thr
1               5

<210> SEQ ID NO 7
<211> LENGTH: 115
<212> TYPE: PRT
<213> ORGANISM: Artificial
<220> FEATURE:
<223> OTHER INFORMATION: IZI-06.1 VH - humanized antibody fragment

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Phe
                20                  25                  30

Tyr Ile Asn Trp Val Arg Gln Ala Pro Gly Gln Gly Leu Glu Trp Ile
            35                  40                  45

Gly Glu Ile Tyr Pro Tyr Ser Gly His Ala Tyr Tyr Asn Glu Lys Phe
        50                  55                  60

Lys Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
            100                 105                 110

Val Ser Ser
        115

<210> SEQ ID NO 8
<211> LENGTH: 113
<212> TYPE: PRT
<213> ORGANISM: Artificial
<220> FEATURE:
<223> OTHER INFORMATION: IZI-06.1 VL - humanized antibody fragment

<400> SEQUENCE: 8

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Thr Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
               100                 105                 110

Arg

<210> SEQ ID NO 9
<211> LENGTH: 288
<212> TYPE: PRT
<213> ORGANISM: Artificial
<220> FEATURE:
<223> OTHER INFORMATION: scFv IZI-06.1 VH-VL - humanized antibody
      fragment

<400> SEQUENCE: 9

Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Gln Ser Gly Ala Glu
                20                  25                  30

Val Lys Lys Pro Gly Ser Ser Val Lys Val Ser Cys Lys Ala Ser Gly
            35                  40                  45

Tyr Thr Phe Thr Asp Phe Tyr Ile Asn Trp Val Arg Gln Ala Pro Gly
    50                  55                  60

Gln Gly Leu Glu Trp Ile Gly Glu Ile Tyr Pro Tyr Ser Gly His Ala
65                  70                  75                  80

Tyr Tyr Asn Glu Lys Phe Lys Ala Arg Val Thr Ile Thr Ala Asp Lys
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Arg Trp Asp Phe Leu Asp Tyr Trp Gly
        115                 120                 125

Gln Gly Thr Thr Val Thr Val Ser Ser Gly Gly Gly Gly Ser Gly Gly
    130                 135                 140

Gly Gly Ser Gly Gly Ser Ala Gln Asp Ile Val Met Thr Gln Ser Pro
145                 150                 155                 160

Leu Ser Leu Pro Val Thr Pro Gly Glu Pro Ala Ser Ile Ser Cys Arg
                165                 170                 175

Ser Ser Gln Ser Leu Leu His Ser Asn Gly Asn Thr Tyr Leu His Trp
            180                 185                 190

Tyr Leu Gln Lys Pro Gly Gln Ser Pro Gln Leu Leu Ile Tyr Thr Val
        195                 200                 205

Ser Asn Arg Phe Ser Gly Val Pro Asp Arg Phe Ser Gly Ser Gly Ser
    210                 215                 220

Gly Thr Asp Phe Thr Leu Lys Ile Ser Arg Val Glu Ala Glu Asp Val
225                 230                 235                 240

Gly Val Tyr Tyr Cys Ser Gln Ser Thr His Val Pro Tyr Thr Phe Gly
                245                 250                 255

Gly Gly Thr Lys Val Glu Ile Lys Arg Ala Ala Ala Glu Gln Lys Leu
            260                 265                 270

Ile Ser Glu Glu Asp Leu Asn Gly Ala Ala His His His His His His
        275                 280                 285

<210> SEQ ID NO 10
<211> LENGTH: 867
<212> TYPE: PRT
<213> ORGANISM: Artificial
<220> FEATURE:

<223> OTHER INFORMATION: scFv IZI-06.1 HSA Fusion protein

<400> SEQUENCE: 10

```
Met Glu Thr Asp Thr Leu Leu Leu Trp Val Leu Leu Trp Val Pro
 1               5                  10                  15

Pro Val Asp Ala Ala Gln Pro Ala Met Ala Gln Val Gln Leu Val Gln
             20                  25                  30

Ser Gly Ala Glu Val Lys Lys Pro Gly Ser Ser Val Lys Val Ser Cys
             35                  40                  45

Lys Ala Ser Gly Tyr Thr Phe Thr Asp Phe Tyr Ile Asn Trp Val Arg
         50                  55                  60

Gln Ala Pro Gly Gln Gly Leu Glu Trp Ile Gly Glu Ile Tyr Pro Tyr
 65                  70                  75                  80

Ser Gly His Ala Tyr Tyr Asn Glu Lys Phe Lys Ala Arg Val Thr Ile
                 85                  90                  95

Thr Ala Asp Lys Ser Thr Ser Thr Ala Tyr Met Glu Leu Ser Ser Leu
            100                 105                 110

Arg Ser Glu Asp Thr Ala Val Tyr Tyr Cys Ala Arg Trp Asp Phe Leu
        115                 120                 125

Asp Tyr Trp Gly Gln Gly Thr Thr Val Thr Val Ser Ser Gly Gly Gly
130                 135                 140

Gly Ser Gly Gly Gly Gly Ser Gly Gly Ser Ala Gln Asp Ile Val Met
145                 150                 155                 160

Thr Gln Ser Pro Leu Ser Leu Pro Val Thr Pro Gly Glu Pro Ala Ser
                165                 170                 175

Ile Ser Cys Arg Ser Ser Gln Ser Leu Leu His Ser Asn Gly Asn Thr
            180                 185                 190

Tyr Leu His Trp Tyr Leu Gln Lys Pro Gly Gln Ser Pro Gln Leu Leu
        195                 200                 205

Ile Tyr Thr Val Ser Asn Arg Phe Ser Gly Val Pro Asp Arg Phe Ser
210                 215                 220

Gly Ser Gly Ser Gly Thr Asp Phe Thr Leu Lys Ile Ser Arg Val Glu
225                 230                 235                 240

Ala Glu Asp Val Gly Val Tyr Tyr Cys Ser Gln Ser Thr His Val Pro
                245                 250                 255

Tyr Thr Phe Gly Gly Gly Thr Lys Val Glu Ile Lys Arg Ala Ala Ala
            260                 265                 270

Gly Gly Ser Gly Gly Asp Ala His Lys Ser Glu Val Ala His Arg Phe
        275                 280                 285

Lys Asp Leu Gly Glu Glu Asn Phe Lys Ala Leu Val Leu Ile Ala Phe
290                 295                 300

Ala Gln Tyr Leu Gln Gln Cys Pro Phe Glu Asp His Val Lys Leu Val
305                 310                 315                 320

Asn Glu Val Thr Glu Phe Ala Lys Thr Cys Val Ala Asp Glu Ser Ala
                325                 330                 335

Glu Asn Cys Asp Lys Ser Leu His Thr Leu Phe Gly Asp Lys Leu Cys
            340                 345                 350

Thr Val Ala Thr Leu Arg Glu Thr Tyr Gly Glu Met Ala Asp Cys Cys
        355                 360                 365

Ala Lys Gln Glu Pro Glu Arg Asn Glu Cys Phe Leu Gln His Lys Asp
370                 375                 380

Asp Asn Pro Asn Leu Pro Arg Leu Val Arg Pro Glu Val Asp Val Met
385                 390                 395                 400

Cys Thr Ala Phe His Asp Asn Glu Glu Thr Phe Leu Lys Lys Tyr Leu
```

-continued

```
                405                 410                 415
Tyr Glu Ile Ala Arg Arg His Pro Tyr Phe Tyr Ala Pro Glu Leu Leu
            420                 425                 430

Phe Phe Ala Lys Arg Tyr Lys Ala Ala Phe Thr Glu Cys Cys Gln Ala
        435                 440                 445

Ala Asp Lys Ala Ala Cys Leu Leu Pro Lys Leu Asp Glu Leu Arg Asp
    450                 455                 460

Glu Gly Lys Ala Ser Ser Ala Lys Gln Arg Leu Lys Cys Ala Ser Leu
465                 470                 475                 480

Gln Lys Phe Gly Glu Arg Ala Phe Lys Ala Trp Ala Val Ala Arg Leu
            485                 490                 495

Ser Gln Arg Phe Pro Lys Ala Glu Phe Ala Glu Val Ser Lys Leu Val
        500                 505                 510

Thr Asp Leu Thr Lys Val His Thr Glu Cys Cys His Gly Asp Leu Leu
    515                 520                 525

Glu Cys Ala Asp Asp Arg Ala Asp Leu Ala Lys Tyr Ile Cys Glu Asn
530                 535                 540

Gln Asp Ser Ile Ser Ser Lys Leu Lys Glu Cys Cys Glu Lys Pro Leu
545                 550                 555                 560

Leu Glu Lys Ser His Cys Ile Ala Glu Val Glu Asn Asp Glu Met Pro
            565                 570                 575

Ala Asp Leu Pro Ser Leu Ala Ala Asp Phe Val Glu Ser Lys Asp Val
        580                 585                 590

Cys Lys Asn Tyr Ala Glu Ala Lys Asp Val Phe Leu Glu Met Phe Leu
    595                 600                 605

Tyr Glu Tyr Ala Arg Arg His Pro Asp Tyr Ser Val Val Leu Leu Leu
610                 615                 620

Arg Leu Ala Lys Thr Tyr Glu Thr Thr Leu Glu Lys Cys Cys Ala Ala
625                 630                 635                 640

Ala Asp Phe His Glu Cys Tyr Ala Lys Val Phe Asp Glu Phe Lys Pro
            645                 650                 655

Leu Val Glu Glu Pro Gln Asn Leu Ile Lys Gln Asn Cys Glu Leu Phe
        660                 665                 670

Glu Gln Leu Gly Glu Tyr Lys Phe Gln Asn Ala Leu Leu Val Arg Tyr
    675                 680                 685

Thr Lys Lys Val Pro Gln Val Ser Thr Pro Thr Leu Val Glu Val Ser
690                 695                 700

Arg Asn Leu Gly Lys Val Gly Ser Lys Cys Cys Lys His Pro Glu Ala
705                 710                 715                 720

Lys Arg Met Pro Cys Ala Glu Asp Tyr Leu Ser Val Val Leu Asn Gln
            725                 730                 735

Leu Cys Val Leu His Glu Lys Thr Pro Val Ser Asp Arg Val Thr Lys
        740                 745                 750

Cys Cys Thr Glu Ser Leu Val Asn Arg Arg Pro Cys Phe Ser Ala Leu
    755                 760                 765

Glu Val Asp Glu Thr Tyr Val Pro Lys Glu Phe Asn Ala Glu Thr Phe
770                 775                 780

Thr Phe His Ala Asp Ile Cys Thr Leu Ser Glu Lys Glu Arg Gln Ile
785                 790                 795                 800

Lys Lys Gln Thr Ala Leu Val Glu Leu Val Lys His Lys Pro Lys Ala
            805                 810                 815

Thr Lys Glu Gln Leu Lys Ala Val Met Asp Asp Phe Ala Ala Phe Val
        820                 825                 830
```

```
Glu Lys Cys Cys Lys Ala Asp Asp Lys Glu Thr Cys Phe Ala Glu Glu
        835                 840                 845

Gly Lys Lys Leu Val Ala Ala Ser Gln Ala Ala Gly Gly His His His
    850                 855                 860

His His His
865

<210> SEQ ID NO 11
<211> LENGTH: 39
<212> TYPE: DNA
<213> ORGANISM: Artificial
<220> FEATURE:
<223> OTHER INFORMATION: Primer A

<400> SEQUENCE: 11
gaccatgatt acgccaagct tccacggca tgcaaattc                           39

<210> SEQ ID NO 12
<211> LENGTH: 39
<212> TYPE: DNA
<213> ORGANISM: Artificial
<220> FEATURE:
<223> OTHER INFORMATION: Primer B

<400> SEQUENCE: 12
acgacggcca gttctagatt aacactctcc cctgttgaa                          39

<210> SEQ ID NO 13
<211> LENGTH: 15
<212> TYPE: PRT
<213> ORGANISM: Artificial
<220> FEATURE:
<223> OTHER INFORMATION: Residue linker

<400> SEQUENCE: 13

Gly Gly Gly Gly Ser Gly Gly Gly Ser Gly Gly Ser Ala Gln
1               5                   10                  15

<210> SEQ ID NO 14
<211> LENGTH: 345
<212> TYPE: DNA
<213> ORGANISM: Artificial
<220> FEATURE:
<223> OTHER INFORMATION: IZI-06.1 VH - humanized antibody fragment VH

<400> SEQUENCE: 14
caggttcagc tggttcagag cggtgcggaa gtgaaaaaac cgggcagcag cgtgaaagtg    60
agctgcaaag cgagcggcta cctttacc gatttctaca ttaactgggt gcgtcaggca     120
ccgggtcagg gcctggaatg gattggcgaa atttatccgt atagcggcca tgcatattac    180
aacgaaaaat caaagcgcg tgtgaccatt accgcggata aaagcaccag caccgcgtat    240
atggaactga gcagcctgcg tagcgaagat accgcggtgt attattgcgc gcgttgggat    300
tttctggatt attggggcca gggcaccacc gttacggtct cgagt                   345

<210> SEQ ID NO 15
<211> LENGTH: 339
<212> TYPE: DNA
<213> ORGANISM: Artificial
<220> FEATURE:
<223> OTHER INFORMATION: IZI-06.1 VL - humanized antibody fragment

<400> SEQUENCE: 15
gatattgtga tgacccagag cccgctgtct ctgccggtca cgccgggtga accggcgagc    60
```

| | |
|---|---|
| attagctgcc gtagcagcca gagcctgctg catagcaacg gcaacaccta tctgcattgg | 120 |
| tatctgcaga aaccgggcca gagcccgcag ctgctgattt ataccgtgag caaccgtttt | 180 |
| agcggcgtgc cggatcgctt tagcggcagc ggtagcggca ccgattttac cctgaaaatt | 240 |
| agccgtgtgg aagcggaaga tgtgggcgtg tattattgca gccagagcac ccatgtgccg | 300 |
| tatacctttg gcggtggcac caaagtggaa attaaacgt | 339 |

<210> SEQ ID NO 16
<211> LENGTH: 867
<212> TYPE: DNA
<213> ORGANISM: Artificial
<220> FEATURE:
<223> OTHER INFORMATION: scFv IZI-06.1 - humanized antibody fragment

<400> SEQUENCE: 16

| | |
|---|---|
| atgaaatacc tattgcctac ggcagccgct ggattgttat tactcgcggc ccagccggcc | 60 |
| atggcccagg ttcagctggt tcagagcggg gcggaagtga aaaaaccggg cagcagcgtg | 120 |
| aaagtgagct gcaaagcgag cggctatacc tttaccgatt ctacattaa ctgggtgcgt | 180 |
| caggcaccgg gtcagggcct ggaatggatt ggcgaaattt atccgtatag cggccatgca | 240 |
| tattacaacg aaaaattcaa agcgcgtgtg accattaccg cggataaaag caccagcacc | 300 |
| gcgtatatgg aactgagcag cctgcgtagc gaagataccg cggtgtatta ttgcgcgcgt | 360 |
| tgggattttc tggattattg gggccagggc accaccgtta cggtctcgag tggtggaggc | 420 |
| ggttcaggcg gaggtggctc tggcggtagt gcacaagata ttgtgatgac ccagagcccg | 480 |
| ctgtctctgc cggtcacgcc gggtgaaccg gcgagcatta gctgccgtag cagccagagc | 540 |
| ctgctgcata gcaacggcaa cacctatctg cattggtatc tgcagaaacc gggccagagc | 600 |
| ccgcagctgc tgatttatac cgtgagcaac cgttttagcg gcgtgccgga tcgctttagc | 660 |
| ggcagcggta gcggcaccga ttttaccctg aaaattagcc gtgtggaagc ggaagatgtg | 720 |
| ggcgtgtatt attgcagcca gagcacccat gtgccgtata cctttggcgg tggcaccaaa | 780 |
| gtggaaatta aacgtgcggc cgcagaacaa aaactcatct cagaagagga tctgaatggg | 840 |
| gccgcacatc accatcatca ccattaa | 867 |

<210> SEQ ID NO 17
<211> LENGTH: 2604
<212> TYPE: DNA
<213> ORGANISM: Artificial
<220> FEATURE:
<223> OTHER INFORMATION: scFv IZI-06.1 HSA fusion protein

<400> SEQUENCE: 17

| | |
|---|---|
| atggagacag acacactcct gctatgggta ctgctgctct gggttccacc ggttgacgcg | 60 |
| gcccagccgg ccatggccca ggttcagctg gttcagagcg gtgcggaagt gaaaaaaccg | 120 |
| ggcagcagcg tgaaagtgag ctgcaaagcg agcggctata cctttaccga tttctacatt | 180 |
| aactgggtgc gtcaggcacc gggtcagggc ctggaatgga ttggcgaaat ttatccgtat | 240 |
| agcggccatg catattacaa cgaaaaattc aaagcgcgtg tgaccattac cgcggataaa | 300 |
| agcaccagca ccgcgtatat ggaactgagc agcctgcgta gcgaagatac cgcggtgtat | 360 |
| tattgcgcgc gttgggattt tctggattat tggggccagg gcaccaccgt tacggtctcg | 420 |
| agtggtggag gcggttcagg cggaggtggc tctggcggta gtgcacaaga tattgtgatg | 480 |

```
acccagagcc cgctgtctct gccggtcacg ccgggtgaac cggcgagcat tagctgccgt    540
agcagccaga gcctgctgca tagcaacggc aacacctatc tgcattggta tctgcagaaa    600
ccgggccaga gcccgcagct gctgatttat accgtgagca accgttttag cggcgtgccg    660
gatcgcttta gcggcagcgg tagcggcacc gattttaccc tgaaaattag ccgtgtggaa    720
gcggaagatg tgggcgtgta ttattgcagc cagagcaccc atgtgccgta ccctttggc     780 ggtggcacca aagtggaaat taaacgtgcg gccgcaggtg gatcaggcgg tgatgcacac    840
aagagtgagg ttgctcatcg gtttaaagat ttgggagaag aaaatttcaa agccttggtg    900
ttgattgcct ttgctcagta tcttcagcag tgtccatttg aagatcatgt aaaattagtg    960
aatgaagtaa ctgaatttgc aaaaacatgt gttgctgatg agtcagctga aaattgtgac   1020
aaatcacttc ataccctttt tggagacaaa ttatgcacag ttgcaactct tcgtgaaacc   1080
tatggtgaaa tggctgactg ctgtgcaaaa caagaacctg agagaaatga atgcttcttg   1140
caacacaaag atgacaaccc aaacctcccc cgattggtga ccagaggt tgatgtgatg     1200 tgcactgctt ttcatgacaa tgaagagaca ttttgaaaa atacttata tgaaattgcc      1260 agaagacatc cttactttta tgccccggaa ctccttttct ttgctaaaag gtataaagct   1320
gcttttacag aatgttgcca agctgctgat aaagctgcct gcctgttgcc aaagctcgat   1380
gaacttcggg atgaagggaa ggcttcgtct gccaaacaga gactcaagtg tgccagtctc   1440
caaaaatttg gagaaagagc tttcaaagca tgggcagtag ctcgcctgag ccagagattt   1500
cccaaagctg agtttgcaga gtttccaag ttagtgacag atcttaccaa agtccacacg    1560
gaatgctgcc atggagatct gcttgaatgt gctgatgaca gggcggacct tgccaagtat   1620
atctgtgaaa tcaagattc gatctccagt aaactgaagg aatgctgtga aaaacctctg    1680
ttggaaaaat cccactgcat tgccgaagtg aaaaatgatg agatgcctgc tgacttgcct   1740
tcattagctg ctgattttgt tgaaagtaag gatgtttgca aaactatgc tgaggcaaag     1800 gatgtcttcc tgggcatgtt tttgtatgaa tatgcaagaa ggcatcctga ttactctgtc   1860
gtgctgctgc tgagacttgc caagacatat gaaaccactc tagagaagtg ctgtgccgct   1920
gcagatcctc atgaatgcta tgccaaagtg ttcgatgaat ttaaacctct tgtggaagag   1980
cctcagaatt taatcaaaca aaattgtgag ctttttgagc agcttggaga gtacaaattc   2040
cagaatgcgc tattagttcg ttacaccaag aaagtacccc aagtgtcaac tccaactctt   2100
gtagaggtct caagaaacct aggaaaagtg ggcagcaaat gttgtaaaca tcctgaagca   2160
aaaagaatgc cctgtgcaga agactatcta tccgtggtcc tgaaccagtt atgtgtgttg   2220
catgagaaaa cgccagtaag tgacagagtc accaaatgct gcacagaatc cttggtgaac   2280
aggcgaccat gcttttcagc tctggaagtc gatgaaacat acgttcccaa agagtttaat   2340
gctgaaacat tcaccttcca tgcagatata tgcacacttt ctgagaagga gagacaaatc   2400
aagaaacaaa ctgcacttgt tgagctcgtg aaacacaagc ccaaggcaac aaaagagcaa   2460
ctgaaagctg ttatggatga tttcgcagct tttgtagaga agtgctgcaa ggctgacgat   2520
aaggagacct gctttgccga ggagggtaaa aaacttgttg ctgcaagtca agctgccggt   2580
ggccaccatc atcaccatca ctaa                                         2604
```

HUTNFR1 SELECTIVE ANTAGONISTS

The present invention relates to a ligand which specifically binds to the human tumor necrosis factor type 1 receptor (huTNFR1), the ligand comprising one or more amino acid sequences of human origin capable of reducing the immunogenic response of the ligand in human beings and one or more amino acid sequences capable of selectively binding to huTNFR1. The present invention further relates to a nucleic acid encoding said ligand and to a pharmaceutical composition for the treatment of disorders connected to huTNFR1.

TNF is a key cytokine regulating inflammation and apoptosis. Depending on the cell type and environmental context, TNF can have opposing effects, immune stimulation or immune suppression, TNF can mediate apoptosis as well as resistance to apoptosis (Locksley et al., Cell, 2001, No. 104, p. 487-501; Aggarwal B. B., Nat. Rev. Immunol., 2003, No. 3, p 745-756). In man, TNF is an essential cytokine regulating the function of the innate immune system and inflammatory responses as a whole, yet has also been recognized as a central pathogenic mediator of a number of chronic and acute diseases. Specifically, in Rheumatoid Arthritis (RA), in inflammatory bowel diseases such as Morbus Crohn and colitis ulcerosa, in psoriasis and in a few rare, inheritable diseases such as Cherubism and periodic fever syndrome, associated with TNF and TNFR1 overexpression, respectively (Chatzantoni K, Mouzaki A., Curr. Top. Med. Chem., 2006, No. 6, p. 1707-1714; Ueki et al., Cell, 2007, No. 128, p. 71-83; Simon A., Van der Meer J. W., Am. J. Physiol. Regul. Integr. Comp. Physiol. 2007, No. 292, p. R86-R98), the TNF system has been identified as the pathologically relevant mediator. In fulminant viral or bacterial infections leading to the so called cytokine syndrom, TNF is known to be critically involved and its crucial role as the mediator of septic shock and multiorgan failure is well documented. TNF has also been implicated in a number of other diseases, in particular metabolic diseases including obesity and type-2 diabetes (Hotamisligil G. S., Nature, 2006, No. 444, p. 860-867; Storz et al., FEBS Lett., 1998, No. 440, p 41-45) and some forms of hepatitis (Kusters et al., Eur. J. Immunol., 1997, No. 27, p. 2870-2875). Moreover, TNF, despite its known therapeutic activity in the local treatment of certain cancers, is considered as a tumor promoter in other malignant diseases, likely via NF-κB mediated apoptosis resistance and other survival pathways (Luo et al., Antibody engineering methods and protocols, 2004, Humana Press, Towota, p. 135-159). Therefore, clinical trials presently also exploit anti TNF strategies as a therapeutic regimen for certain hematologic malignancies (e.g. AML). From a mechanistic point of view, it has been demonstrated in numerous models including TNFR knock-out mice that TNFR1 is the major mediator of TNF's pathological phenotypes (Locksley et al., Cell, 2001, No. 104, p 487-501; Aggarwal et al., Nat. Rev. Immunol., 2003, No. 3, p. 745-756).

In several chronic inflammatory diseases TNF neutralizing reagents, specifically anti TNF antibodies and soluble TNFR-Fc fusion proteins, are clinically widely applied. Three drugs are approved that interfere with TNF action: Remicade (Vilcek and Feldmann, 2004) (Centocor/Tanabe), Enbrel (Immunex/Wyeth) and Humira (Celltech/Abbott). The drugs all target TNF itself. The drugs are approved for treatment of rheumatoid arthritis (RA), juvenile RA, psoriatic arthritis, Crohn's disease and ankylosing spondylitis. TNF targeting drugs show great success in RA, but the therapeutic effect is only for a restricted time period, and some patients are a priori refractory to anti TNF antibody treatment or develop resistance. Further, the outcome of clinical trials with CDP571, a humanized TNF specific monoclonal antibody, e.g. in Morbus Crohn, are certainly less promising then expected, demanding development of new concepts and reagents targeting the TNF/TNFR system.

Besides an expected general immune suppression, the approved anti TNF drugs show additional side effects such as the production of anti-dsDNA antibodies, lupus and neuroinflammatory disease. The immune suppressed status of patients under general TNF blockade is associated with increased risk of infectious diseases, including commensal organisms. In the "Lenercerpt study" (1999), clinical trials of an anti-TNF agent for treatment of MS had to be stopped because the disease status became worse, not better. The mechanistic background for this at that time unexpected adverse response is now clearer and related to the differential role of TNFR1 and TNFR2 in this disease, with TNFR1 signals propagating neuronal death and TNFR2 signals activating myelin sheet regeneration. Altogether, as outlined below there is increasing evidence that new therapeutic strategies aiming at a receptor selective targeting of TNF action should in many cases be superior to a general blockade of TNF signalling. For example, in some animal disease models detailed below, the contradictory effects of TNF action are explained by a differential function of the distinct receptors, TNFR1 and TNFR2. The gained knowledge on the mechanisms of action of TNF at the receptor level now indeed opens up new therapeutic strategies aiming at a pharmacological blockage of one of the receptors, thus potentially resulting in more specific effects.

For instance, retinal ischemia is a complication of diabetes where retinal neurons undergo TNF-induced apoptosis to cause blindness. Retinas of TNFR2 knockout mice show increased apoptosis, but the retinas of TNFR1 knockout mice show decreased apoptosis compared to the wild type (Fontaine et al., J. Neurosci., 2002, No. 22, RC216).

Similarly, EAE is an animal model of multiple sclerosis (MS). It is characterized by an initial autoimmune inflammation directed against myelin. The myelin-specific reaction later subsides but other epitopes take over as autoimmune antigens. While TNF knock-out mice show a weaker initial inflammatory reaction to myelin, the myelin-specific immune reaction does not subside. In TNFR1-knockout mice, the initial inflammatory reaction is equally reduced, but it then subsides, indicating that TNFR2 is sufficient to mediate the long-term immunosuppressive function of TNF, while the inflammatory reaction is mediated by TNFR1 (Kassiotis G., Kollias G., J. Exp. Med., 2001, No. 193, p. 427-434; Kollias et al., Curr. Dir. Autoimmun., 2002, No. 5, p. 30 to 50; Owens et al., Nat. Med., 2001, No. 7, p. 161-166).

Likewise, in a mouse model of toxin (cuprizone) induced, reversible CNS demyelination, resembling the demyelination/regeneration phases in multiple sclerosis (MS), there is compelling evidence that the remyelination process upon toxin withdrawal is TNF dependent and selectively requires TNFR2 signaling, triggering oligodendrocyte progenitor expansion and differentiation into mature myelin sheet forming oligodendrocytes (Arnett et al., Nat. Neurosci., 2001, No. 4, p. 1116-1122). These findings of TNF dependence of oligodendrocyte regeneration mirror the situation in humans suffering from MS: In clinical trials aiming at complete TNF blockade in MS with a TNFR1-Fc fusion protein, the blocking of TNF was associated with aggravation of disease rather then therapeutic benefit, which is in accordance with the results of the animal model described above.

Moreover, for instance cortical neurons of mice succumb to excitotoxic death upon overt triggering of the NMDA receptor by neurotransmitter glutamate. Glutamate is released from dying tissue upon ischemic conditions (Oxygen deprivation) such as occurring in stroke. Primary cultures of neurons can be made fully resistant to excitotoxicity in a TNFR2 dependent manner involving a PI3K-AKT-NF-κB pathway. By contrast, TNFR1 signals enhance glutamate induced cell death (Marchetti et al., J. Biol. Chem., 2004, No. 279, p. 32869-32881), indicating a differential role of TNFR1 and TNFR2 in the CNS.

Therefore, in various models of both acute and chronic neurodegeneration, retinal ischemia, stroke models and in Multiple Sclerosis, a complete block of TNF has no apparent therapeutic effects but rather is directly detrimental or reduces regenerative capacity of the affected tissue. Accordingly, specific blocking of TNFR1, the inflammatory TNFR, and maintenance of TNFR2 function, presents a promising therapeutic approach for these diseases.

Likewise, both in Rheumatoid Arthritis (RA), in psoriasis and in more rare, inheritable diseases such as Cherubism and periodic fever syndrome, associated with TNF and TNFR1 overexpression, respectively, TNFR1 is considered or has been clearly identified as the pathologically relevant receptor. A differential role of TNFR1 and 2 becomes also apparent in Morbus Crohn, in which only a fraction of the patients respond to anti TNF therapeutics, and in SLE (Komata et al., Tissue Antigens, 1999, No. 53, p. 527-533), with resistance to treatment and disease susceptibility, respectively, both correlating with TNFR2 mutation(s).

Accordingly, using receptor selective antibody to target TNFR1 represents an alternative to established anti TNF strategies in these chronic inflammatory diseases. This appears of particular relevance in patients becoming refractory to anti TNF reagents upon repeated treatment cycles. Moreover, as global and continued blocking of TNF is associated with a functional deficiency in the innate and adaptive immune response, the risk of complications due to infectious diseases is considerably increased in theses patients. Selective interference with TNFR1 maintains TNF responses via TNFR2, which should be of benefit for the overall immune competence of the patients.

Support for a selective TNFR1 blockade as a powerful therapeutic regimen comes from previous studies of the inventors on the in vitro and in vivo function of the antagonistic mouse monoclonal antibody (mab) H398 specific for human TNFR1 (Thoma et al., J. Exp. Med., 1990, No. 172, p. 1019-1023; Grell et al., Cell, 1995, No. 83, p. 793-802; Moosmayer et al., Ther. Immunol., 1995, No. 2, p. 31-40). This murine antibody and its recombinant mouse scFv derivatives are capable to neutralize a wide spectrum of TNF activities in vitro through competitive inhibition of TNF binding to human TNFR1; the mab was shown to be effective in preventing bacterially induced lethal shock syndrom in baboons, where H398 shows crossreactivity with the TNFR1 of this species. The therapeutic efficacy of antibody H398 in TNF dependent, chronic diseases cannot be evaluated in clinical trials due to mouse origin of the antibody, bearing the risk of acute adverse reactions towards the mouse antibody and/or the rapid development of an immune response upon repeated treatment cycles.

Therefore, a need exists for novel substances which should effectively and specifically interact with human TNFR1 (huTNFR1) as TNF-antagonists in a patient and which should have a reduced (i.e. tolerable) immunogenic response upon administration to human beings.

Thus, the technical problem underlying the present invention is to provide novel low-immunogenic huTNFR1-ligands as antagonists of TNF action suitable for application in human beings as a therapeutic for treatment of a variety of TNF mediated disorders.

According to the present invention, the above-described problem is solved by providing a huTNFR1-ligand comprising a proteinaceous construct having (i) one or more amino acid sequences of human origin capable of reducing the immunogenic response of said huTNFR1-ligand in humans, and (ii) one or more amino acid sequences of non-human origin capable of selectively binding to huTNFR1.

Herein, the term "huTNFR1-ligand" means any molecule or group of molecules which can selectively bind the human TNF type 1 receptor (huTNFR1) and at the same time shows a reduced immunogenic response when administered to a human being. By binding to huTNFR1, said huTNFR1-ligand acts as an antagonist to TNF and lymphotoxin alpha (LTα) which are the natural ligands inter alia of TNFR1.

The term "huTNFR1" used herein does not only relate to the human TNF type 1 receptor as such, but does also include any portion thereof, or any other receptor which is structurally and/or functionally related to the huTNFR1.

The expression "reduced immunogenic response" means an immunogenic response which is reduced as compared to the immunogenic response of a huTNFR1-ligand comprising exclusively amino acid sequences of non-human origin. Examples of huTNFR1-ligands comprising exclusively amino acid sequences of non-human origin include peptides, proteins and nucleic acids of non-human mammal origin, such as rodent origin, for example a murine antibody.

The expression "proteinaceous construct" used herein is not specifically restricted and means any molecule or group of molecules which contains one or more peptide bonds, preferably peptide sequences, and binds to huTNFR1 while showing a reduced immunogenic response in a human being. The proteinaceous construct according to the present invention may further comprise nucleic acids and organic and inorganic compounds, such as sugars or fatty acids. Further, the proteinaceous construct may comprise a group of molecules which are independently associated via covalent or non-covalent bonds, such as fusion proteins. According to another embodiment of the present invention, the proteinaceous construct may further be coupled with additional molecules, for example polyethyleneglycol or methoxy-polyethylenglycol, i.e. it might be PEGylated.

The huTNFR1-ligand and/or the proteinaceous construct according to the present invention may be produced by any suitable method known to the person skilled in the art, such as for example by recombinant methods involving the construction of a suitable plasmid or vector and expression in a microorganism or in any higher organism, or by automated peptide synthesis, such as solid phase peptide synthesis.

The expression "amino acid sequences of human origin" used herein means such amino acid sequences which can be found in the human body. However, the expression is not only restricted to such amino acid sequences which can exactly be found in the human body but also include those amino acid sequences which have a similarity of 50% or higher with human amino acid sequences. Specific examples of amino acid sequences of human origin are the amino acid sequences contained in a human antibody or a fragment thereof.

Moreover, the expression "amino acid sequences of non-human origin" used herein means any amino acid sequence, which can be found in a non-human animal, such as a non-human mammal. For example, the amino acid sequence of non-human origin may be a sequence of a non-human antibody, for example a murine antibody.

In the proteinaceous construct of the present invention the advantages of amino acid sequences of human origin, which reduce the risk of e.g. immunogenicity in a patient, are combined with the selectivity towards huTNFR1 of amino acid sequences of non-human origin, such as for example of those found in the murine antibody H398.

According to another embodiment of the huTNFR1-ligand as defined above the proteinaceous construct comprises a humanized antibody or at least one fragment thereof.

The term "antibody" used herein means any kind of antibody which can bind to an antigen, including natural antibodies, mutated antibodies and (semi)-synthetic antibodies, as long as the antibody allows an administration to a human being with a reduced immunogenic response thereto. In a preferred embodiment, the antibody or fragment thereof is a humanized antibody obtainable by e.g. recombinant nucleic acid technology ("humanized recombinant antibody") or at least one fragment thereof or an antibody-like recombinant protein. As an example, without limitation thereto, a fragment may be contained in an antibody like recombinant protein such as diabodies, scFv-Fc fusion proteins, and scFv-CH3 fusion proteins.

The antibody, or at least one fragment thereof, or an antibody-like recombinant protein, may contain one or more mutations or variations, such as added, deleted or substituted amino acids or nucleic acids, as long as it has no negative effect on the interaction with huTNFR1. Further, the antibody or at least one fragment thereof, or an antibody-like recombinant protein, may contain one or more mutations or variations, such as added, deleted or substituted amino acids or nucleic acids, which have a positive effect on the interaction of huTNFR1 and which improve the antagonistic activity of said molecule. In particular, such mutated variants have a better affinity and/or a better inhibitory activity.

According to the present invention, the term "fragment" means any portion of an antibody as defined above as long as it has the ability to bind to the desired antigen through one (monovalent) or two (bivalent) antigen (huTNFR1) binding sites. Moreover, a fragment of the present invention may comprise several different portions from said antibody. Examples of proteolytically or recombinantly produced monovalent fragments of an antibody include antigen binding fragment (Fab), single chain variable fragment (scFv), variable fragment (Fv), disulfide-stabilized Fv (dsFv), variable domain of the immunoglobulin heavy chain (VH), variable domain of the immunoglobulin light chain (VL), complementary determining regions (CDRs), and combinations thereof. Examples of proteolytically processed or recombinant bivalent fragments of the present invention include F(ab)$_2$, diabodies, scFv-Fc fusion proteins, and scFv-CH3 fusion proteins.

For example, the antibody or the at least one fragment thereof may be a humanized antibody or at least one fragment thereof derived from the murine antibody H398.

There is no limitation as to the technique of humanization of the antibody, as long as the antibody binds to the desired antigen. Examples of humanization include, without limitation thereto, complementarity determining region grafting (CDR grafting) (Jones et al. 1986, Nature 321, 522-525), specificity determining residue grafting (SDR grafting) (Kashmiri et al., 2005, Methods 36, 25-34), resurfacing of variable domains (Roguska et al., 1994, Proc. Natl. Acad. Sci. USA 91, 969-973), structure-based selection and humanization by CDR grafting (Hwang et al., 2005, Methods 36, 35-42), and deImmunization strategies (Hellendorn et al., 2004, Cancer Cell International 4 (Sppl. I), 20).

The expression "humanized antibody" used herein means any antibody in which protein engineering is used to reduce the amount of foreign ("non-human") protein sequence by swapping e.g. rodent antibody constant regions and/or variable-domain frameworks or framework residues with sequences that are found in human antibodies.

In a specific embodiment of the present invention, the proteinaceous construct of the above-defined huTNFR1-ligand may be a humanized antibody, which contains amino acid sequences of human origin and such of non-human, e.g. rodent origin.

The term "scFv" used herein means a fusion of the variable regions of the heavy and light chains of any immunoglobulin, linked together with a linker, such as for example a peptide composed of serine, glycine, or any other natural or non-natural amino acid.

In a further embodiment of the huTNFR1-ligand as defined above, the at least one fragment is selected from the group consisting of a Fab-region, a scFv, a genetically engineered or post-translationally processed recombinant derivative of said fragments, and a chemically modified derivative of said fragments.

According to a specific embodiment of the above-defined huTNFR1-ligand, the at least one fragment is a scFv comprising the amino acid sequence according to SEQ ID NO.: 9.

In a further embodiment of the huTNFR1-ligand as defined above, the proteinaceous construct comprises one or more of the complementary determining regions (CDRs) selected from the group, consisting of SEQ ID NOs: 1 to 6, or parts thereof, conferring binding to huTNFR1, wherein said CDRs are preferably contained in the one or more amino acid sequences of non-human origin capable of selectively binding to huTNFR1 as outlined under (ii) of the proteinaceous construct, above.

The CDRs of the above-defined huTNFR1-ligand, such as those of SEQ ID NOs: 1 to 6, may be present in any combination, for example two, three, four, five or six of said CDRs may be present. Additionally, multiple copies or genetic variants of any of the CDRs may be present in the huTNFR1-ligand of the present invention, as long as the ligand shows sufficient affinity towards human TNFR1 and allows a reduced immunogenic response when administered to a human being.

According to a specific embodiment of the huTNFR1-ligand, the proteinaceous conctruct comprises the amino acid sequence according to SEQ ID NO.: 7 as variable domain of the heavy chain (VH) and the amino acid sequence according to SEQ ID NO.: 8 as variable domain of the light chain (VL).

In yet another embodiment of the present invention, the above-defined huTNFR1-ligand comprises an additional tag allowing specific interaction with a biologically acceptable compound. There is not a specific limitation with respect to the tag usable in the present invention, as far as it has no or tolerable negative impact on the binding of the huTNFR1-ligand to huTNFR1 or the immunogenic response when administered to a human being. Examples of suitable tags include His-tag, Myc-tag, FLAG-tag, Strep-tag, Calmodulin-tag, GST-tag, MBP-tag, and S-tag.

In another embodiment of the huTNFR1-ligand as defined above, the proteinaceous construct further comprises a biologically acceptable compound non-covalently bound thereto or covalently bound thereto by posttranslational chemical conjugation or by recombinant gene technology.

The expression "biologically acceptable compound" used herein is not specifically restricted and means any compound usable in a biological environment, such as in a living organism, including also pharmaceutical acceptance of said biologically acceptable compound. Examples of the biologically acceptable compounds according to the present invention are, without any limitation thereto, peptides, proteins, nucleic acids, carbohydrates, lipids, as well as other organic and inorganic compounds. The biologically acceptable compound preferably exerts additional positive effects, for example improved biochemical/biophysical properties, such as enhanced solubility, prolonged stability, improved antagonistic activity, and improved pharmacokinetic properties, such as increased in vivo half-life, increased tissue penetration, blood brain barrier passage and reduced toxicity.

According to one specific embodiment aiming at improving pharmacokinetic properties of the above-defined huTNFR1-ligand, the biologically acceptable compound is selected from the group consisting of serum proteins.

In another embodiment of the huTNFR1-ligand as defined above the biologically acceptable compound is albumin. According to a specific embodiment, the biologically acceptable compound is human serum albumin (HSA).

In a further embodiment of the above-defined huTNFR1-ligand, the biologically acceptable compound comprises an albumin-binding domain (e.g. from bacteria), an albumin-binding peptide composed of natural or non-natural amino acids, one or more acyl chains with albumin-binding activity, polyethylene glycol or methoxy-polyethylene glycol. In yet a further embodiment of the above-defined huTNFR1-ligand, the biologically acceptable compound comprises another antibody or fragment thereof specific for a serum protein component or a natural or synthetic ligand, which binds to a serum component (e.g. albumin).

In a further specific embodiment aiming at improving pharmacokinetic properties of the above-defined huTNFR1-ligand, the biologically acceptable compound comprises another antibody targeting a cell surface molecule or extracellular matrix component. As an example, anti-HIR (human Insulin receptor) or anti-TR (Transferrin receptor) antibodies have been used for active transport via the blood-brain-barrier and delivery of compounds into the brain (Boado et al., 2007, Bioconjug. Chem., Epub ahead of press).

In a further specific embodiment aiming at improving the functional activity of the above-defined huTNFR1-ligand, the biologically acceptable compound comprises an antibody which binds to another epitope of TNFR1, distinct from that recognized by the above defined huTNFR1 ligand, thereby increasing overall binding (avidity) and selectivity of this bispecific reagent.

According to another specific embodiment of the huTNFR1-ligand as defined above, the proteinaceous construct comprises a fusion protein according to SEQ ID NO.: 10.

A further aspect of the present application relates to a nucleic acid encoding the above-defined huTNFR1-ligand.

The nucleic acid according to the present invention is not specifically restricted and may contain DNA or RNA. The nucleic acid may further comprise sequences which are used in detection or isolation procedures, such as for example fluorescence labels or His-tag. The nucleic acid may further comprise artificial building blocks such as artificial DNA, RNA or PNA building blocks. Moreover, the nucleic acid according to the present invention may be produced in any suitable way, such as recombinantly or by chemical synthesis, such as solid phase synthesis.

Another aspect of the present invention relates to a vector comprising the nucleic acid sequence as defined above. The vector of the present invention is not specifically restricted as long as it can be used in the transfection of a suitable host cell and is suitable for heterologous gene expression.

Methods used to construct vectors are well known to a person skilled in the art and described in various publications. In particular, techniques for constructing suitable vectors, including a description of the functional components such as promoters, enhancers, termination and polyadenylation signals, selection markers, origins of replication, splicing signals, and leader sequence, are reviewed in considerable details in (Sambrook et al., 1989) and references cited therein. Vectors may include, without any limitation thereto, plasmid vectors, phagemids, cosmids, articificial/mini-chromosomes (e.g. ACE), MAR vectors, or viral vectors such as baculovirus, retrovirus, adenovirus, adeno-associated virus, herpes simplex virus, retroviruses, bacteriophages. Examples of vectors suitable for prokaryotic expression include pAB1. (Kontermann et al., 1997). The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing cloning sites into which one or more polynucleotides can be operatively linked, are well known in the art and some are commercially available from companies such as Stratagene, La Jolla, Calif.; Invitrogen, Carlsbad, Calif.; Promega, Madison, Wis.; BD Biosciences Clontech, Palo Alto, Calif.; Lonza Biologics PLC, Slough, Berkshire, England. Examples of eukaryotic vectors are pcDNA3, pSecTag, and pEE 6.4.

In a preferred embodiment the expression vector comprises at least one nucleic acid sequence which is a regulatory sequence necessary for transcription and translation of nucleotide sequences that encode for a peptide/polypeptide/protein of interest.

A further aspect of the present invention relates to a host cell containing the above-defined nucleic acid or the above-defined vector. The host cell of the present invention is not specifically restricted and includes all cells usable in the production of the huTNFR1-ligand and/or the proteinaceous construct or parts thereof. Examples of host cells suitable for the present invention include prokaryotic cells and eukaryotic cells, such as yeast, plant cells, insect cells, and mammalian cells of different species origin and whole transgenic organisms (transgenic plants, transgenic animals). Examples of prokaryotic cells include *E. coli*, TG1, and *Pseudomonas* spec. Examples of animal cells include hamster cells, preferably BHK21, BHK TK-, CHO, CHO-K1, CHO-DUKX, CHO-DUKX B1, and CHODG44 cells or the derivatives/progenies of any of such cell line. In a further embodiment of the present invention host cells are murine myeloma cells, preferably NS0 and Sp2/0 cells or the derivatives/progenies of any of such cell line. Examples of mammalian cells which can be used for expression of huTNFR1 ligands according to the present invention are summarized in Table 1.

TABLE 1

Eukaryotic production cell lines

| CELL LINE | ORDER NUMBER |
|---|---|
| NS0 | ECACC No. 85110503 |
| Sp2/0-Ag14 | ATCC CRL-1581 |
| BHK21 | ATCC CCL-10 |
| BHK TK- | ECACC No. 85011423 |
| HaK | ATCC CCL-15 |
| 2254-62.2 (BHK-21 derivative) | ATCC CRL-8544 |
| CHO | ECACC No. 8505302 |
| CHO wild type | ECACC 00102307 |
| CHO-K1 | ATCC CCL-61 |
| CHO-DUKX(= CHO duk-, CHO/dhfr-) | ATCC CRL-9096 |
| CHO-DUKX B11 | ATCC CRL-9010 |
| CHO-DG44 | (Urlaub et al., 1983) |
| CHO Pro-5 | ATCC CRL-1781 |
| V79 | ATCC CCC-93 |
| B14AF28-G3 | ATCC CCL-14 |
| HEK 293 | ATCC CRL-1573 |
| COS-7 | ATCC CRL-1651 |

TABLE 1-continued

Eukaryotic production cell lines

| CELL LINE | ORDER NUMBER |
|---|---|
| U266 | ATCC TIB-196 |
| HuNS1 | ATCC CRL-8644 |
| CHL | ECACC No. 87111906 |

Host cells are most preferred, when being established, adapted, and completely cultivated under serum free conditions, and optionally in media which are free of any protein/peptide of animal origin. Commercially available media such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), CHO-S-Invtirogen), serum-free CHO Medium (Sigma), and protein-free CHO Medium (Sigma) are exemplary appropriate nutrient solutions. Any of the media may be supplemented as necessary with a variety of compounds examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics and trace elements. Any other necessary supplements may also be included at appropriate concentrations that would be known to those skilled in the art. In the present invention the use of serum-free medium is preferred, but media supplemented with a suitable amount of serum can also be used for the cultivation of host cells. For the growth and selection of genetically modified cells expressing the selectable gene a suitable selection agent is added to the culture medium.

Moreover, there is provided a pharmaceutical composition comprising a therapeutically effective amount of the huTNFR1-ligand as defined above and optionally one or more additional components selected from the group consisting of a pharmaceutically acceptable carrier, pharmaceutically acceptable salts, an auxiliary agent, a stabilizer, a diluent and a solvent, or any combination thereof.

According to another embodiment the pharmaceutical composition as defined above, is usable for the treatment of rheumatoid arthritis, psoriasis, Morbus Crohn, colitis ulcerosa and other chronic inflammatory and/or autoimmune diseases, acute fulminant viral or bacterial infections, metabolic diseases, acute neurodegenerative diseases, chronic neurodegenerative diseases, preferably selected from multiple sclerosis, Parkinson and Alzheimer's disease, genetically inherited diseases with TNF/TNFR1 as the causative pathologic mediator, preferably selected from periodic fever syndrome and Cherubism, and cancer.

The huTNFR1-ligand of the present invention may further be used in the preparation of a medicament for the treatment of any TNF-related disorder, such as those mentioned above.

There is further provided a method for treating a patient suffering from a disease selected from rheumatoid arthritis, psoriasis, Morbus Crohn, colitis ulcerosa and other chronic inflammatory and/or autoimmune diseases, acute fulminant viral or bacterial infections, metabolic diseases, acute neurodegenerative diseases, chronic neurodegenerative diseases, preferably selected from multiple sclerosis, Parkinson and Alzheimer's disease, genetically inherited diseases with TNF/TNFR1 as the causative pathologic mediator, preferably selected from periodic fever syndrome and Cherubism, and cancer, comprising the step of administering a therapeutically effective amount of the above-defined huTNFR1-ligand to a patient in need thereof.

According to the present invention the huTNFR1-ligand as defined above may be used for the procedure of guided selection according to the state of the art (Jespers et al., 1994, Biotechnology) for isolation of a functionally equivalent huTNFR1 specific antibody from human immunoglobulin gene libraries, thus further minimizing potential immunogenicity of said reagent.

Therefore, according to another aspect of the present invention, a huTNFR1-ligand is provided comprising a proteinaceous construct having (i) one or more amino acid sequences of human origin capable of reducing the immunogenic response of said huTNFR1-ligand in humans, and (ii) one or more amino acid sequences capable of selectively binding to huTNFR1, obtainable by guided selection using a proteinaceous construct as defined above as a template.

Further, a process is provided for the production of a huTNFR1-ligand having a reduced immunogenic response when administered to a human being, comprising the steps of (a) providing a proteinaceous construct as defined above, (b) identifying one or more amino acid sequences of human origin capable of binding selectively to huTNFR1 by guided selection using one or more of the amino acid sequences of said proteinaceous construct, particularly the amino acid sequences of non-human origin, as a template, and (c) constructing said ligand comprising at least one or more of the amino acid sequences identified under step (b).

Figure 5A:
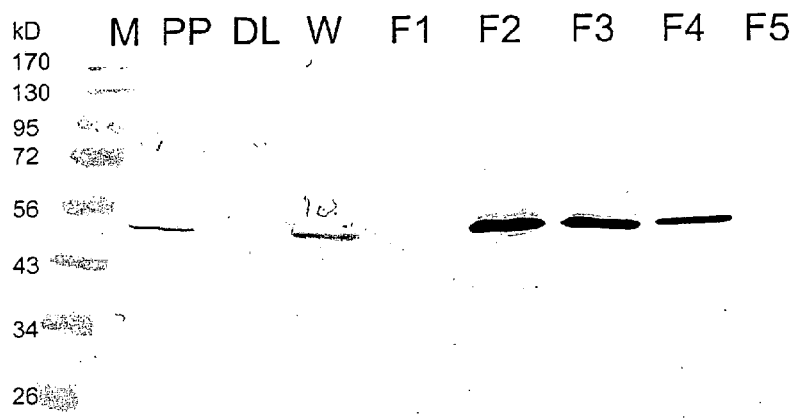

Another aspect of the present invention relates to a use of a huTNFR1-ligand comprising a proteinaceous construct having (i) one or more amino acid sequences of human origin capable of reducing the immunogenic response of said huTNFR1-ligand in humans, and (ii) one or more amino acid sequences of non-human origin capable of selectively binding to huTNFR1, as template for guided selection in the identification and construction of another low-immunogenic huTNFR1-ligand comprising amino acid sequences which are essentially or only of human origin.

THE FIGURES SHOW

FIG. 1 shows the alignment of mouse monoclonal antibody H398 $V_H$ and $V_L$ sequences, the closest human germline sequences for $V_H$ (VH1-69=1-e=DP-88) and $V_L$ (A3=DPK15), as well as the humanized $V_H$ and $V_L$ sequences (IZI-06.1 VH, IZI-06.1 VL) generated by CDR-grafting. Amino acids differing between H398 and the human germline sequences are marked with asterisks. Framework regions (FR) and complementarity determining regions (CDRs) are indicated.

FIG. 2 shows the DNA sequences of codon-optimized IZI-06.1 VH and IZI-06.1 VL (upper lane) and corresponding amino acids (lower lane); the italic characters at the beginning and at the end of each amino acid sequence do not belong to IZI-06.1 VH and IZI-06.1 VL and relate to amino acid sequences used for cloning/processing and contain cleavage sites for certain restriction enzymes.

FIG. 3 shows the superimposed model structures of H398 Fv (light gray) and IZI-06.1 Fv (dark gray) backbone. a) side view of the two model structures. b) top view of the CDR regions H1-H3 and L1-L3. Models were generated with WAM (Whitelegg and Rees, 2000) WAM—an improved algorithm for modelling antibodies on the Web. Prot. Eng. 13, 819-824). Structures were visualized with Pymol (DeLano Scientific, San Carlos, Calif., USA).

FIG. 4 shows a cloning strategy to generate a bacterial vector for the expression of Fab fragments.

FIG. 5a shows a Western Blot on nitrocellulose after SDS PAGE using a non reducing 12% gel after IMAC (1) preparation. Detection via anti human Fab-AP, AP staining according to standard procedures, 15 μL samples were applied to the gel. Abbreviations: PP=Periplasm extract, DL=Flow through IMAC, W=Wash fraction, F=Fraction.

Figure 5B:
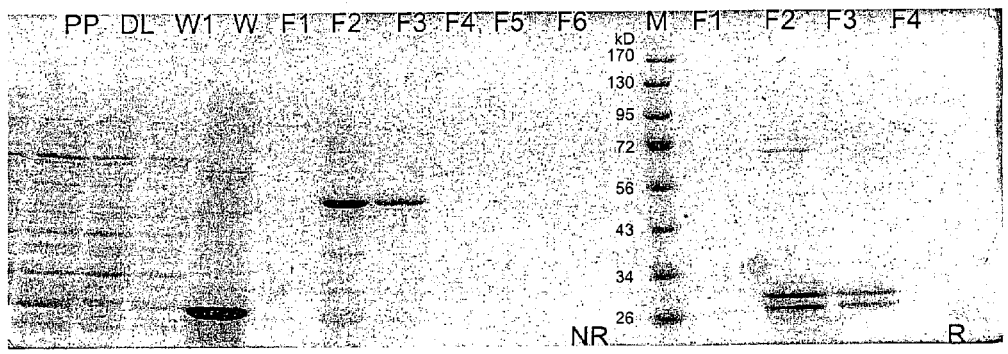

FIG. 5b shows a Coomassie staining of an IMAC (1) purification after SDS PAGE on a 12% gel. The left part from the marker represents a non-reducing gel, the right part a gel under reducing conditions. Sample volume was 15 μL.

Figure 6:
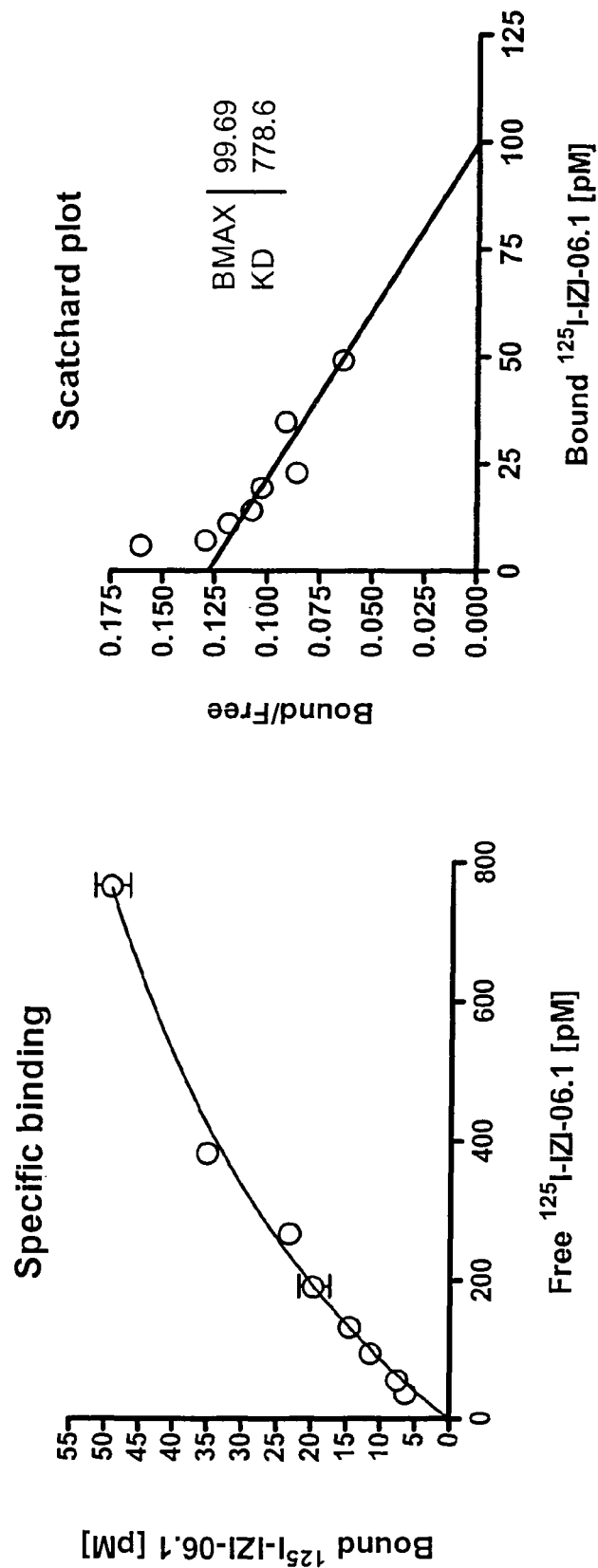

FIG. 6 shows a saturation binding curve and the derived Scatchard plot of IZI-06.1-Fab binding to receptor positive cells. Nonspecific binding has been subtracted. The resulting data show that IZI-06.1-Fab binding to TNFR1-Fas is saturable and specific, with an apparent affinity of $K_D$=0.778 nM.

Figure 7:
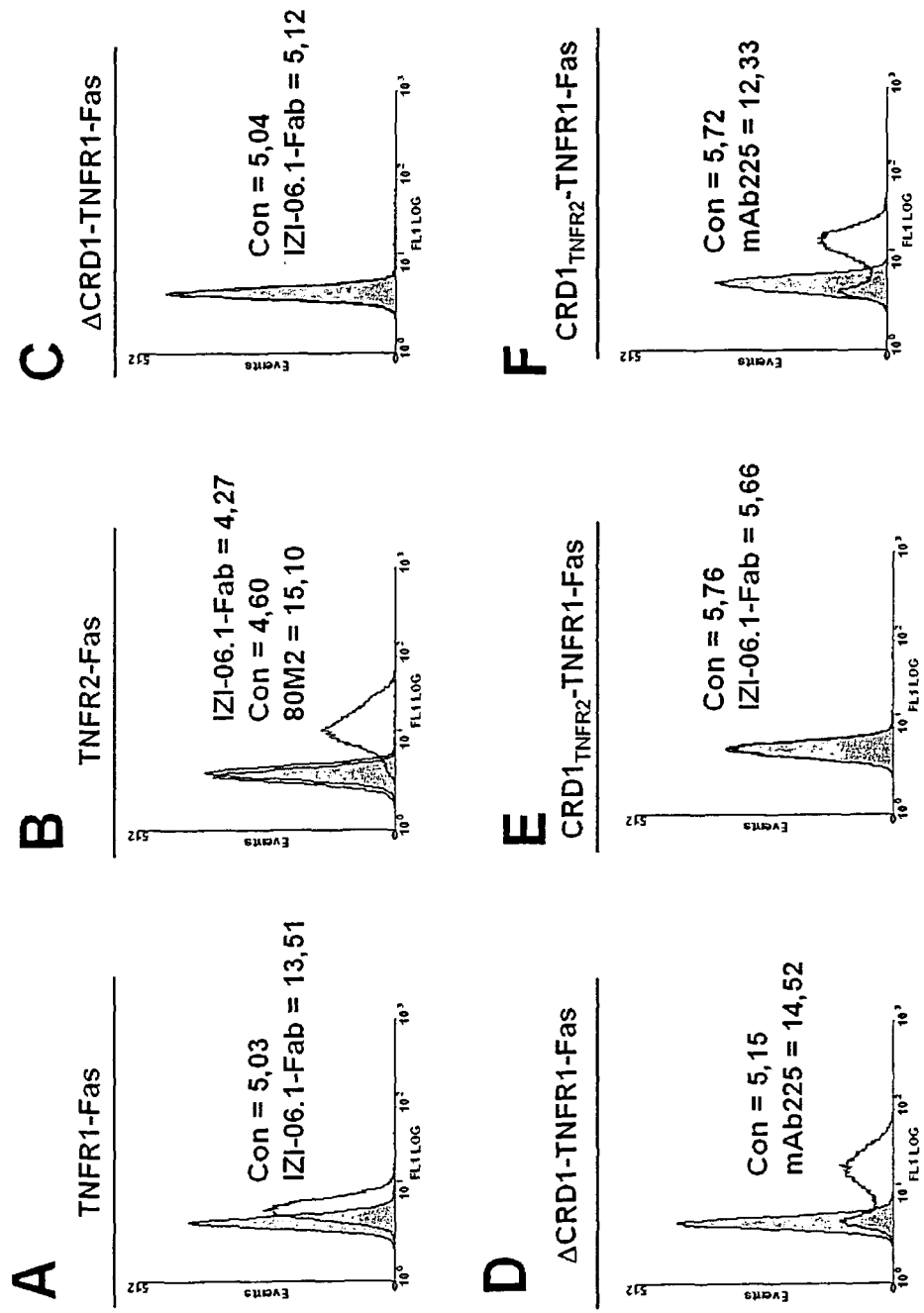

FIG. 7 shows flow cytometry analyses of mouse embryonic fibroblasts that stably express chimeric receptors comprised of the extracellular domain (ED) of TNFR1 and the cytoplasmic domain of death receptor Fas, TNFR1-Fas (A), or chimeric receptors comprised of TNFR2-ED and Fas (TNFR2-Fas) (B), or chimeric receptors with a deletion of cystein rich domain (CRD) 1 of TNFR1, ΔCRD1-TNFR1-Fas (C and D) or a CRD1 exchange mutant, comprised of a TNFR1-Fas molecule containing the CRD1 of TNFR2, CRD1$_{TNFR2}$-TNFR1-Fas (E and F). These transfectants were incubated on ice for two hours with 2.5 μg/ml of IZI-06.1-Fab (A-C, E, white histograms), the TNFR1-specific antibody mAb225 (D and F, white histograms), the TNFR2-specific antibody 80M2 (B, white+bold histogram) or were only treated with secondary antibodies as control (gray histograms). The incubation buffer was PBA (PBS+0.05% bovine serum albumin+0.02% NaN3). Cells were incubated with FITC-labeled secondary antibodies (80M2 and mAb225: Goat anti-murine IgG; IZI-06.1 Fab: Goat anti-HIS-tag) and cells were analyzed by flow cytometry. Cells were gated for viable cells and total fluorescence intensities (MnX) are given for each antibody. (Con=control values).

Figure 8:
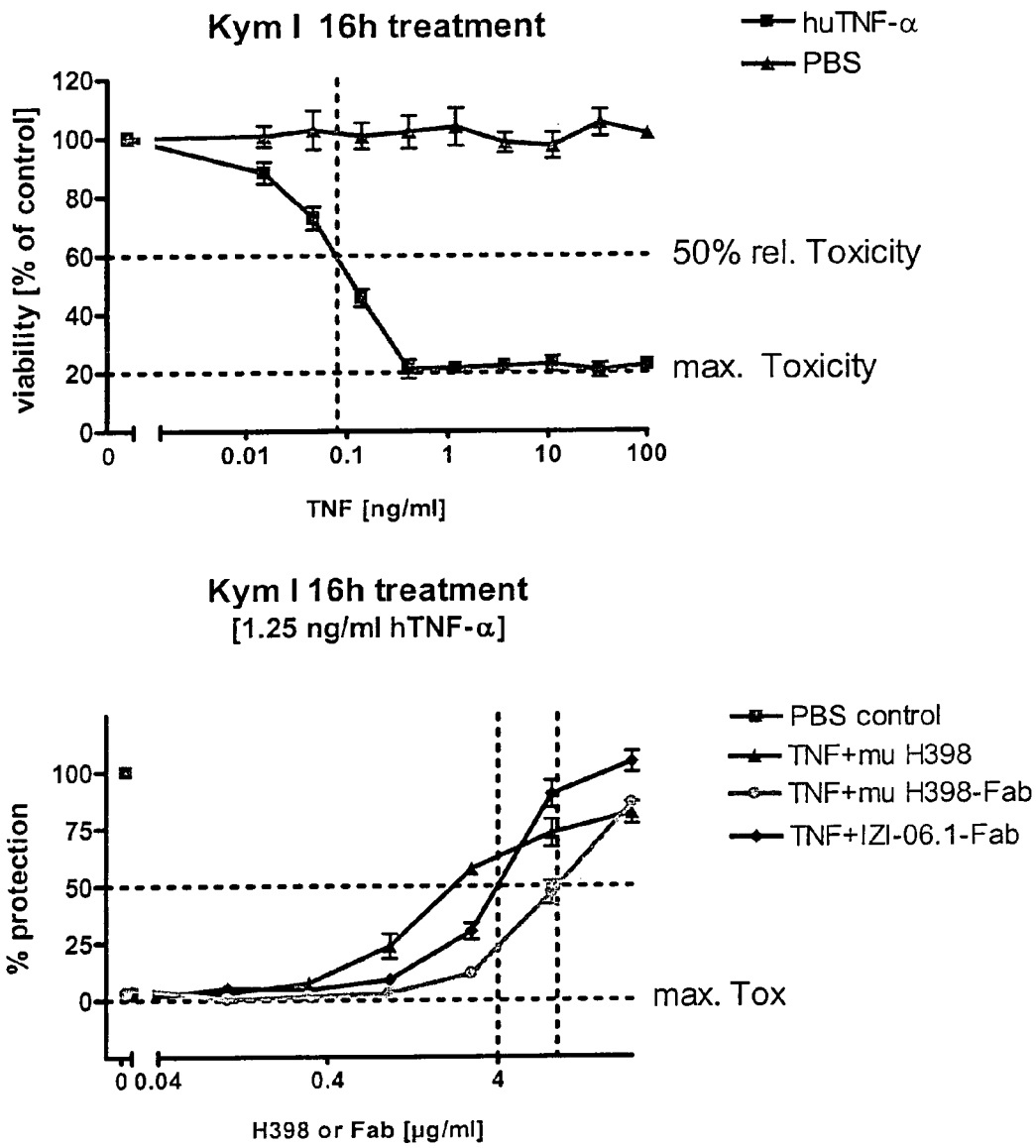

FIG. 8 shows diagrams relating to TNFR1 inhibition by IZI-06.1. Kym I cells were seeded one day before treatment in a 96-well plate (10.000 cells/well in RPMI1640+5% FCS). Next day cells were treated with 100 ng/ml huTNF in trifold dilution steps. Control was titration of PBS. After 16 hours cells were analyzed by cristal violet assay. OD absorbance was measured at 550 nm. Results are displayed as percent of control (PBS treated cells). Upper panel: 1.25 ng/ml huTNF was estimated as a dose sufficient to induce maximum toxicity. Lower panel: A constant amount of 1.25 ng/ml huTNF—was applied after preincubation for 60 min with 25 μg/ml H398, H398-Fab or humanized H398-Fab, all diluted in trifold steps. After 16 hours cells were analyzed by cristal violet assay. OD absorbance was measured at 550 nm. Results are displayed as percent of control.

Figure 9:
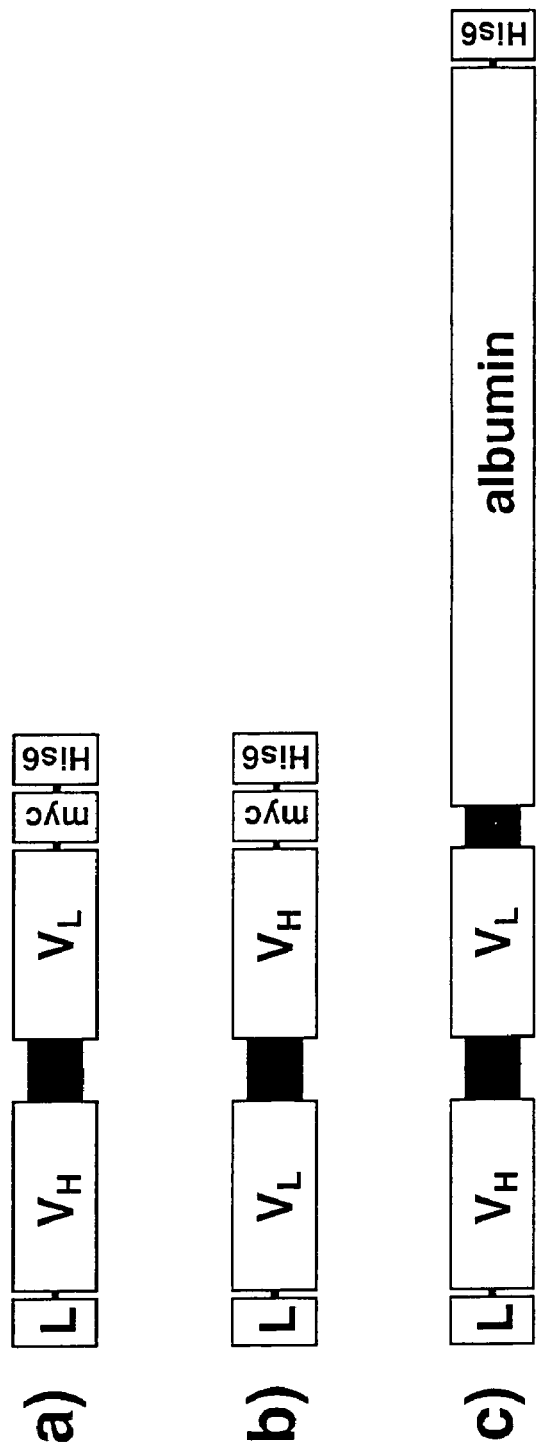

FIG. 9 shows the composition of scFv IZI-06.1 in the $V_H$-$V_L$ (a) and $V_L$-$V_H$ (b) configuration as well as a scFv-albumin fusion protein (c). All constructs contain a N-terminal leader sequence for soluble expression as well as a hexa-histidyl-tag (His6) and in case of scFv molecules also a myc-tag. Linker sequences are shown as black bars.

The huTNFR1-ligand according to the present invention binds to human TNFR1 with high specificity, interacting with the CRD1 of this receptor. Unexpectedly, the huTNFR1-ligand binds TNFR1 with a very high affinity, advantageously exceeding that of the murine antibody H398. Thus, the human TNFR1 ligand as described above very efficiently prevents the action and bioactivity of the naturally occurring ligands for TNFR1, TNF and LTα and is superior in its antagonistic activity to the murine H398 antibody described in prior art. Due to the content of amino acid sequence(s) of human origin this ligand is of advantageously low immunogenicity. Thus, the huTNFR1-ligand of the present invention allows the treatment of a patient suffering from a disorder connected to TNFR1 without the risk of acute adverse reactions towards the ligand and/or the rapid development of an immune response, while at the same time benefiting from the high selectivity and blocking efficiency of the amino acid sequence of non-human origin directed against huTNFR1.

The present invention will be further illustrated in the following examples, without any limitation thereto.

EXAMPLES

Example 1

In Silico Generation of an Anti-TNF Receptor 1 Antagonist Based on Mouse Monoclonal Antibody H398 Sequences and Human Germ Line Ig V Gene Sequences The amino acid sequences of H398 heavy chain variable domain ($V_H$) and light chain variable domain ($V_L$) (Moosmayer et al., Ther. Immunol., 1995, No. 2, p. 31-40) was used to search for similar human germline V segments using the V base database (http://vbase.mrc-cpe.cam.ac.uk/) as well as IgBlast. This search identified several $V_H$ germline sequences (DP75, DP8, DP88) with 61.2-62.2% overall similarity and several $V_L$ germline sequences (DPK15, DPK13, DPK27, DPK28) with 80.0-81.0% similarity. The identified sequences were aligned with H398 $V_H$ and $V_L$ and amino acids critical for CDR conformation, the $V_H$/$V_L$ interface as well as the Vernier zone were identified as described (O'Brien S., Jones T., Antibody engineering, a lab manual, Springer, 2001, p. 567-590; Lo B. K. C., Antibody engineering, methods and protocols, Humana Press, 2004, p. 135-159). CDR regions were assigned using the definitions of Kabat, Chothia, AbM and Contact (Martin A. C. R., Antibody engineering, a lab manual, Springer, 2001, p. 422-439). Furthermore, canonical classes of L1-L3 and H1-H2 were determined as following: L1-4, L2-1, L3-1, H1-1, H2-3 (Martin A. C. R., Antibody engineering, a lab manual, Springer, 2001, p. 567-590). For CDR replacement, the CDRs were defined as following: amino acids L24-L34 (CDRL1), L46-L56 (CDRL2), L89-L97 (CDRL3), H26-H35 (CDRH1), H47-H65 (CDRH3), and H95-H102 (CDRH33). As human acceptor sequences, we chose $V_H$ germline segment VH1-69 (1-e, DP88) and $V_L$ germline segment A3 (DPK15). All six CDRs were inserted into these human variable germline segments (FIG. 1). The resulting unique sequences were designated IZI-06.1 VH (SEQ ID NO.: 7) and IZI-06.1 VL (SEQ ID NO.: 8), respectively.

Example 2

Synthesis of DNA Sequence of IZI-06.1 VH and IZI-06.1 VL

Codon-optimized DNA encoding the two humanized variable domains (IZI-06.1 VH, (SEQ ID NO.: 7), IZI-06.1 VL (SEQ ID NO.: 8)) was synthesized by GeneArt (Regensburg, Germany) adding appropriate cloning sites (FIG. 2).

Example 3

Model Structures of H398 and IZI-06.1 Fv Fragments

Model structures of H398 and IZI-06.1 Fv are generated using the Web Antibody Modelling server (WAM)

(Whitelegg N. R. J., Rees A. R., Web. Prot. Eng., 2000, No. 13, p. 819-824). An alignment of the two model structures reveals high concordance of the protein backbone and side chain conformation including the CDRs, with the exception of CDRH3, which show a slight distortion (FIG. 3). Thus, Asp96 at the tip of CDRH3 of H398 model and IZI-06.1 model has moved approximately 0.38 nm out of the antigen-binding pocket.

Example 4

Cloning of IZI-06.1 and Construction of a Monovalent Ig Fragment (Fab Format)

The genes encoding the variable heavy and light chain domain ($V_H$, $V_L$) of antibody IZI-06.1 are synthesized by GeneArt and supplied in vector pPCR-Script (pPCR-Script-IZI-06.1-$V_H$, pPCR-Script-IZI-06.1-$V_L$) containing appropriate cloning sites. For cloning of the Fd fragment ($V_H$-$C_H$1) (=construct pAB1-IZI-06.1-Fd) plasmid pPCR-Script-IZI-06.1-$V_H$ is digested with restriction enzymes SfiI and XhoI and the resulting fragment is cloned into vector pAB1-$C_H$1 (containing the gene for the $C_H$1 domain of the human immunoglobulin γ1 heavy chain) digested with the same enzymes. For cloning of the light chain ($V_L$-$C_L$) (=construct pAB1-IZI-06.1-L) plasmid pPCR-Script-IZI-06.1-$V_L$ is digested with restriction enzymes SfiI and AscI and the resulting fragment is cloned into vector pAB1-$C_H$1 (containing the gene for the human $C_?$ domain) digested with the same enzymes. The light chain gene including the vector encoded ribosome binding site (RBS) and the pelB leader sequence is amplified by PCR from plasmid pAB1-IZI-06.1-L using primers A (5'-GAC CAT GAT TAC GCC AAG CTT TCC ACG GCA TGC AAA TTC-3') (SEQ ID NO.: 11) and B (5'-ACG ACG GCC AGT TCT AGA TTA ACA CTC TCC CCT GTT GAA-3') (SEQ ID NO.: 12). With this step a HindIII and a XbaI site are introduced at the 5' and 3' end, respectively. The PCR product is digested with restriction enzymes HindIII and XbaI and cloned into plasmid pAB1-IZI-06.1-Fd digested with the same enzymes. This results in a final bacterial expression plasmid pAB1-IZI-06.1-Fab encoding a Fab fragment of antibody IZI-06.1 including a hexahistidyl-tag at the C-terminus of the Fd fragment.

Example 5

Expression System

Vector: pAB1 (Kontermann et al., 1997)
Cells: *E. coli* TG1 (Stratagene, La Jolla, U.S.A.)
Basic
Principle: Expression of IZI-06.1 Fab is under control of $P_{Lac}$ and induced by IPTG according to standard procedures. Selection is achieved through addition of Ampicillin (bla-Gen).
 The N-terminal peLB leader sequence allows periplasmatic expression of the target gene product, the former being removed from the target protein through proteolytic processing in the periplasm. Target protein (IZI-06.1) is isolated as soluble protein upon destabilisation of bacterial cell wall with EDTA and Lysozyme. The remaining bacterial cells are osmotically stabilised as spheroblasts with Saccharose/$MgSO_4$ buffer to avoid cell lysis and cells are separated by centrifugation.

Expression:
Procedure: Batch, shaking flask culture.
Pre culture: 50 mL LB-Medium plus 100 μg/mL Ampicillin and 1% Glucose, inoculated with a single *E. coli* colony. Incubation ON at 30° C. on a rocking platform (125 rpm).
Main
culture: 1 L LB-Medium plus 100 μg/mL Ampicillin and 0.1% Glucose, inoculated with 5% (V/V) pre-culture. Incubation at 30° C. on a rocking platform (125 rpm). At $OD_{600}$ (~3 h incubation time) induction of protein expression by addition of IPTG (1 mM final concentration). Expression time was 3.5 h at 25° C.
Extraction: Spin down culture for 10 min at 4000 g. Resuspend pellets in 50 mL periplasma solubilisation buffer PPA (PPA: 30 mM Tris-HCl, 1 mM EDTA, 20% Saccharose). Add 50 μg/mL Lysozyme and incubate suspension for 30 min on ice. Spheroblasts are then removed by centrifugation at 18.000 g. The supernatant (periplasma extract) is dialysed ON with 200×Vol. PBS.
The typical yield of this expression/extraction protocol is ~1-2 mg Fab IZI-06.1/L culture.

Example 6

Purification

Basic
Principle: Three step purification protocol with two consecutive IMAC runs followed by size exclusion chromatography (SEC). IZI-06.1 carries a C-terminal myc-His-Tag (see pAB1, Cloning strategy). First and second purification step is IMAC (Immobilised Metal-ion Affinity Chromatography). Histidine residues within the His-Tag bind specifically to ligand-chelated Ni-Ions on a Sepharose Matrix. The second IMAC step is for concentrating the product. SEC is performed in a semi-preparative manner using FPLC (Pharmacia, Germany). This step separates according to apparent MW and allows the separation of higher MW aggregates of the target protein as well as higher and lower MW protein and non protein contaminants. Specifically, misfolded an/or nonprocessed target protein IZI-06.1 shows apparent higher MW in SEC and can be separated from correctly folded, bioactive product.
IMAC (1):
Column: HiTrap 5 mL (Ni-Ion chelating) (Amersham Pharmacia).
Application: 4×50 mL periplasmatic extract (dialysed).
Flow rate: 0.5-1.0 mL/min
Wash
fraction: 25 mM Sodium-phosphate-buffer pH 8.0; 0.5 M NaCl; 25 mM Imidazol, 5×$V_{(column)}$.
Elution: 25 mM Sodium phosphate-buffer pH 8.0; 0.5 M NaCl; 500 mM Imidazol
Fractions: 8×3.5 mL
 IZI-06.1 elutes predominantly in fractions 2 and 3 (FIGS. 5a, 5b). Fractions 2-4 were pooled and dialysed against 500×Vol. PBS. The resulting dialysate is concentrated by a second IMAC step (IMAC 2).
IMAC (2):
Column: HisTrap 1 mL (Ni-Ion chelating) (Amersham Pharmacia).
Application: 2×3 mL dialysed fractions from IMAC (1) (2 runs).
Flow rate: 0.5-1.0 mL/min
Wash
fraction: 25 mM Sodium-phosphate-buffer pH 8.0; 0.5 M NaCl; 25 mM Imidazol, 5×$V_{(column)}$.

Elution: 25 mM Sodium phosphate-buffer pH 8.0; 0.5 M NaCl; 500 mM Imidazol
Fraction: 8×1.0 mL
SEC/FPLC:
column: Superdex 200 (Pharmacia)
Eluent: PBS (steril filtered)
Application: 200 μL of fraction 2 or 3 from IMAC(2)
Flow rate: 0.25 mL/min
Fractions: Nr. 1-5: 1 mL, Nr. 5-35: 0.5 mL
  IZI-06.1 Fab is mainly present in fractions 24/25 (active Fab by bioassay) and in small amount in fractions 20/21 (less active Fab, likely predominantly missfolded protein).

Example 7

Functional activity of IZI-06.1 Fab

Binding characteristics, determination of binding affinity by equilibrium binding studies:

For the determination of the affinity to TNFR1, saturation binding studies at 4° C. with radioactively labelled IZI-06.1Fab are performed. The antibody is labelled with $^{125}$Iodine using the chloramine T method. In brief, 10 μg of purified protein are incubated in phosphate buffer (pH 7.4) at room temperature with $3.7 \times 10^7$ Becquerel of Na$^{125}$I together with chloramine T. The reaction is stopped with Na-disulfite and excess NaI and labelled proteins are separated by gel-filtration using a PD10 column (Pharmacia). One milliliter fractions are collected. The protein eluted in fractions 2 and 3, free $^{125}$I is detected in fractions 7 to 9. The resulting protein concentration is 2.7 μg/ml and radioactivity is 120.000 cpm/ng. Bioactive material is determined by incubating constant amounts of labelled IZI-06.1 Fab with increasing numbers of TNFR1-Fas expressing mouse fibroblast cells. The resulting hyperbolic curve is used to fit a one-site binding equation by linear regression and the extrapolated maximal binding value ($B_{max}$) represents the percentage of bioactive material (approx. 10%). Data from this analysis are used to calculate the applied antibody concentrations in the following experiments.

To determine the affinity ($K_D$ value) of IZI-06.1 Fab, 200.000 TNFR1-Fas positive cells are incubated on ice for three hours with increasing concentrations of labelled IZI-06.1 (2.5-50 ng in a total volume of 150 μl). As binding buffer, phosphate buffered saline+2% fetal calf serum+0.02% NaN$_3$ is used. Non-specific binding is determined by co-incubating cells with the 180-fold respective concentration of unlabelled IZI-06.1. Bound $^{125}$I-Fab is determined with a gamma-counter and resulting data is used to fit a one-site binding hyperbola that contains the saturation binding constant $K_D$:

$$\text{Bound} = (B_{max} \times [IZIFab])/([IZIFab] + K_D)$$

The goodness of data is evaluated by performing a linearization transformation, also known as Scatchard plot. The resulting data show that IZI-06.1 binding to TNFR1 is saturable and specific, with an apparent affinity of $K_D$=0.778 nM.

Binding characteristics, TNFR1 selectivity and epitope mapping by receptor domain swapping/deletion and FACS analyses:

A His-tag positive IZI-06.1-Fab is used to determine specificity of TNFR1 binding or TNFR1-Fas binding, respectively as well as for characterization of the epitope recognized by the antibody derivative. FIG. 7A shows an indirect immunofluorescence flow cytometry analysis. IZI-06.1-Fab positively stains TNFR1-Fas chimera expressing cells in comparison to the negative control (detection reagent: FITC-labeled His-specific antibody. The comparably low intensity of the staining in comparison to indirect IF with TNFR1 specific mab225 (FIG. 7D) is known to be largely due to the different secondary detection reagents used (His-tag specific detection antibody versus anti mouse-Ig detection antibody). No specific binding occurs on TNFR2-Fas expressing cells in comparison to the negative control, the TNFR2-specific antibody 80M2 served as a positive control (FIG. 7B). No specific staining occurs on a cell positive for TNFR1-Fas constructs, where the membrane distal cysteine rich domain (CRD) 1 has been removed (FIG. 7C). This construct, however, is readily detected by another TNFR1-specific mab, mab225 (FIG. 7D). Further, no specific staining occurs on a cell expressing a functional (signal competent) TNFR1-Fas construct, where the membrane distal CRD1 has been replaced by that of TNFR2 (FIG. 7E). Again, this receptor chimera is readily detected by the mab225, known to bind TNFR1 outside of CRD1. Data shown in FIG. 7C-F therefore allow to conclude that IZI-06.1 recognizes the CRD1 of TNFR1. The inventors know that CRD1 is critically involved in TNF binding through influencing the conformation of CRD2, the latter providing, together with CRD3, one of the direct ligand contact site (unpublished data of the inventors).

Inhibition of TNF Action:

Purified IZI-06.1 Fab is tested for antagonistic activity in a Kym-1 human rhabdomyo-sarcoma cell line model, which is highly TNF sensitive (LD50 below 100 pg/ml sTNF, no inhibition of protein synthesis required) and responds through both TNFR1 and TNFR2 (the latter signal pathway was previously shown to induce via NF-κB signaling endogeneous TNF expression and subsequently autotropic signaling of apoptosis of the membrane expressed TNF via TNFR1, (Grell at al., EMBO J., 1999, No. 18, p. 3034-3043). Antagonistic activity of IZI-06.1 Fab is compared with murine mab H398 and enzymatically prepared Fab from H398. FIG. 8 shows efficient and complete block of TNF mediated cytotoxic action on Kym-1 cells by IZI-06.1 Fab, at a two to fourfold lower concentration as compared to H398 Fab. The full length mab, as expected from previous results, shows a higher neutralizing activity compared to monovalent Fabs at lower concentrations, likely due to lower off rate of the divalent reagent (higher avidity). Importantly, mab H398 does not reach complete block of TNF activity in this sensitive in vitro assay, because of conversion from an antagonist into a partial agonist at high concentrations. This is explained by dose dependent increase in TNFR crosslinking, thus potentially forming ligand independent, functional TNFR signaling complexes (see also Moosmayer et al., Ther. Immunol., 1995, No. 2, p. 31-30)

In summary, according to the present invention, one of the surprising and unexpected key features is that TNFR1 specific antagonist IZI-06.1 Fab displays superior TNFR1 blocking activity compared to an existing murine Fab of same specificity and is superior to a full length mab because of complete lack of receptor crosslinking capability, i.e. IZI-06.1 Fab is devoid of any intrinsic signaling potential and thus a veritable antagonist of TNFR1.

Example 8

Single-Chain Fv IZI-06.1 and Derivatives Thereof

Cloning and Expression of scFv IZI-06.1 ($V_H$-$V_L$):
ScFv IZI-06.1 ($V_H$-$V_L$) is generated by a two-step cloning into phagemid vector pHEN2 introducing a vector encoded 15 residue linker (GGGGSGGGGSGGSAQ) (SEQ ID NO.: 13) as well as a N-terminal pelB leader sequence and a C-terminal myc-tag and hexahistidyl-tag (His6). For soluble expression the scFv encoding sequence is obtained by digestion of pHEN2-scFv IZI-06.1 ($V_H$-$V_L$) plasmid DNA with restriction enzymes SfiI and NotI and cloning of the resulting fragment into expression vector pAB1 digested with the same enzymes. Expression and purification is performed as follows: 2 L of 2×TY, 100 µg/mL ampicillin, 0.1% glucose are inoculated with 20 ml overnight culture of transformed TG1 and grown to exponential phase ($OD_{600}$=0.8) at 37° C. Protein expression is induced by addition of 1 mM IPTG and bacteria are grown for additional 3 h at RT. Cells are harvested by centrifugation and resuspended in 100 ml of 30 mM Tris-HCl, pH 8.0, 1 mM EDTA, 20% sucrose. After addition of 5 mg lysozyme, cells are incubated for 15-30 min on ice. After addition of 10 mM $Mg_2SO_4$, cells are centrifuged at 10.000 g for 30 min, 4° C. Supernatant is dialyzed against PBS and loaded onto a Ni-NTA column (Qiagen, Hilden, Germany) equilibrated with 50 mM sodium phosphate buffer, pH 7.5, 500 mM NaCl, 20 mM imidazole. After a washing step (50 mM sodium phosphate buffer, pH 7.5, 500 mM NaCl, 35 mM imidazole) the His-tagged recombinant antibody fragments are eluted with 50 mM sodium phosphate buffer, pH 7.5, 500 mM NaCl, 100 mM imidazole. Protein fractions are pooled and dialyzed against PBS. Protein concentration is determined spectrophotometrically and calculated using the calculated e-value of each protein.

Cloning and Expression of a scFv IZI-06.1-Albumin Fusion Protein:

A scFv IZI-06.1 ($V_H$-$V_L$) human albumin fusion protein (SEQ ID NO.: 10) is generated by cloning DNA encoding scFv IZI-06.1 ($V_H$-$V_L$) from plasmid pAB1 as SfiI-NotI fragment into plasmid pSecTagA-HSA containing the cDNA encoding human albumin. The plasmid DNA is transfected with Lipofectamine™2000 (Invitrogen, Karlsruhe, Germany) into HEK293 cells. Stable transfectants are generated by selection with zeocin (300 µg/ml). Cells are expanded and grown in RPMI, 5% FCS to 90% confluence. For protein production cells are cultured in Opti-MEM (Invitrogen, Karlsruhe, Germany) replacing media every 3 days for 3-4 times. Supernatants are pooled and proteins are concentrated by ammonium sulfate precipitation (60% saturation), before loading onto a Ni-NTA column (Qiagen, Hilden, Germany). Purification by IMAC is performed as described above.

The invention claimed is:

1. An isolated huTNFR1-antagonist, comprising a proteinaceous construct comprising a humanized antibody or at least one fragment thereof having
   (i) one or more amino acid sequences of human origin capable of reducing the immunogenic response of said huTNFR1-antagonist in humans, and
   (ii) one or more amino acid sequences of non human origin capable of selectively binding to huTNFR1 thereby completely blocking the TNFR1 activity,
   wherein the proteinaceous construct comprises the amino acid sequence according to SEQ NO.: 7 as variable domain of the heavy chain (VH) and the amino acid sequence according to SEQ ID NO.: 8 as variable domain of the light chain (VL), or a fragment of a humanized antibody, wherein the fragment is a scFv comprising the amino acid sequence according to SEQ ID NO.: 9.

2. The huTNFR1-antagonist according to claim 1, wherein the proteinaceous construct reaches complete block of the TNFR1 activity in a Kym-1 human rhabdomyosarcoma cell line model.

3. The huTNFR1-antagonist according to claim 1, comprising an additional tag allowing specific interaction with a biologically acceptable compound.

4. The huTNFR1-antagonist according to claim 1, the proteinaceous construct further comprises a biologically acceptable compound non-covalently bound thereto or covalently bound thereto by posttranslational chemical conjugation or by recombinant gene technology.

5. The huTNFR1-antagonist according to claim 4, wherein the biologically acceptable compound is a serum protein.

6. The huTNFR1-antagonist according to claim 4, wherein the biologically acceptable compound is albumin.

7. The huTNFR1-antagonist according to claim 4, wherein the proteinaceous construct comprises a fusion protein with human serum albumin according to SEQ ID NO.: 10.

8. A composition comprising a therapeutically effective amount of the huTNFR1-antagonist according to claim 1 and optionally one or more additional components selected from the group consisting of a pharmaceutically acceptable carrier, pharmaceutically acceptable salts, an auxiliary agent, a stabilizer, a diluent and a solvent, or any combination thereof.

9. A pharmaceutical composition comprising a therapeutically effective amount of the huTNFR1-antagonist according to claim 8.

* * * * *